US012377168B2

(12) United States Patent
Khanna

(10) Patent No.: US 12,377,168 B2
(45) Date of Patent: Aug. 5, 2025

(54) GENE THERAPIES FOR USHER SYNDROME (USH1B)

(71) Applicant: University of Massachusetts, Boston, MA (US)

(72) Inventor: Hemant Khanna, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 961 days.

(21) Appl. No.: 17/604,572

(22) PCT Filed: Apr. 16, 2020

(86) PCT No.: PCT/US2020/028489
§ 371 (c)(1),
(2) Date: Oct. 18, 2021

(87) PCT Pub. No.: WO2020/214797
PCT Pub. Date: Oct. 22, 2020

(65) Prior Publication Data
US 2022/0175967 A1    Jun. 9, 2022

Related U.S. Application Data

(60) Provisional application No. 62/836,414, filed on Apr. 19, 2019.

(51) Int. Cl.
*C07K 14/47* (2006.01)
*A61K 48/00* (2006.01)

(52) U.S. Cl.
CPC ........ *A61K 48/005* (2013.01); *C07K 14/4716* (2013.01)

(58) Field of Classification Search
CPC .................. A61K 48/005; C07K 14/4716
See application file for complete search history.

(56) References Cited

U.S. PATENT DOCUMENTS

| | | | |
|---|---|---|---|
| 2016/0076054 A1 | 3/2016 | Auricchio et al. |
| 2019/0017048 A1 | 1/2019 | Van Wyk |
| 2021/0087583 A1 | 3/2021 | van Wyk et al. |
| 2022/0202959 A1 | 6/2022 | Khanna |

FOREIGN PATENT DOCUMENTS

| | | |
|---|---|---|
| CN | 105209619 A | 12/2015 |
| EP | 0725136 A1 | 8/1996 |
| ES | 2704677 T3 | 3/2019 |
| WO | WO 2013/075008 A1 | 5/2013 |
| WO | WO 2014/140051 A1 | 9/2014 |
| WO | WO 2014/170480 A1 | 10/2014 |
| WO | WO 2016/005514 A1 | 1/2016 |
| WO | WO 2016/139321 A1 | 9/2016 |
| WO | WO 2018/055134 A1 | 3/2018 |
| WO | WO 2018/187552 A9 | 10/2019 |

OTHER PUBLICATIONS

Aparisi et al. "Study of USH1 splicing variants through minigenes and transcript analysis from nasal epithelial cells." PLoS One 8.2 (2013): e57506. (Year: 2013).*
Extended European Search Report for Application No. 20791702.2, mailed Feb. 10, 2023.
Invitation to Pay Additional Fees for Application No. PCT/US2020/028489, mailed Jul. 9, 2020.
International Search Report and Written Opinion for Application No. PCT/US2020/028489, mailed Sep. 2, 2020.
International Preliminary Report on Patentability for Application No. PCT/US2020/028489, mailed Sep. 2, 2020.
Invitation to Pay Additional Fees for Application No. PCT/US2020/028487, mailed Jul. 9, 2020.
International Search Report and Written Opinion for Application No. PCT/US2020/028487, mailed Sep. 2, 2020.
International Preliminary Report on Patentability for Application No. PCT/US2020/028487, mailed Sep. 2, 2020.
Chen et al., Molecular cloning and domain structure of human myosin-VIIa, the gene product defective in Usher syndrome 1B. Genomics. Sep. 15, 1996;36(3):440-8. doi: 10.1006/geno.1996.0489.
De Oliveira et al., Herpes simplex virus type 1/adeno-associated virus hybrid vectors. Open Virol J. Jun. 18, 2010;4:109-22. doi: 10.2174/1874357901004030109.
Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.
Fuster-Garcia et al., USH2A Gene Editing Using the CRISPR System. Mol Ther Nucleic Acids. Sep. 15, 2017;8:529-541. doi: 10.1016/j.omtn.2017.08.003. Epub Aug. 12, 2017.
Garcia-Garcia et al., Mutational screening of the USH2A gene in Spanish USH patients reveals 23 novel pathogenic mutations. Orphanet J Rare Dis. Oct. 17, 2011;6:65. doi: 10.1186/1750-1172-6-65.
Hashimoto et al., Lentiviral gene replacement therapy of retinas in a mouse model for Usher syndrome type 1B. Gene Ther. Apr. 2007;14(7):584-94. doi: 10.1038/sj.gt.3302897. Epub Feb. 1, 2007.
Lopes et al., Retinal gene therapy with a large MYO7A cDNA using adeno-associated virus. Gene Ther. Aug. 2013;20(8):824-33. doi: 10.1038/gt.2013.3. Epub Jan. 24, 2013.

(Continued)

*Primary Examiner* — Emily A Cordas
(74) *Attorney, Agent, or Firm* — Wolf, Greenfield & Sacks, P.C.

(57) ABSTRACT

Aspects of the disclosure relate to compositions and methods useful for delivering minigenes to a subject. Accordingly, the disclosure is based, in part, on isolated nucleic acids and gene therapy vectors, such as viral (e.g., rAAV) vectors, comprising one or more gene fragments encoding a therapeutic gene product, such as a protein or peptide (e.g. a minigene). In some embodiments, the disclosure relates to gene therapy vectors encoding a USH1B protein (e.g. the gene product of USH1B, also referred to as MYO7A) or a portion thereof. In some embodiments, compositions described by the disclosure are useful for treating diseases associated with mutations in the USH1B (MYO7A) gene, for example Usher Syndrome.

15 Claims, 1 Drawing Sheet
Specification includes a Sequence Listing.

(56) References Cited

OTHER PUBLICATIONS

Rebeh et al., Reinforcement of a minor alternative splicing event in MYO7A due to a missense mutation results in a mild form of retinopathy and deafness. Mol Vis. Sep. 30, 2010;16:1898-906.
Slijkerman et al., Antisense Oligonucleotide-based Splice Correction for USH2A-associated Retinal Degeneration Caused by a Frequent Deep-intronic Mutation. Mol Ther Nucleic Acids. Nov. 1, 2016;5(10):e381. doi: 10.1038/mtna.2016.89.
Weston et al., Genomic structure and identification of novel mutations in usherin, the gene responsible for Usher syndrome type IIa. Am J Hum Genet. Apr. 2000;66(4):1199-210. doi: 10.1086/302855. Epub Mar. 22, 2000. Erratum in: Am J Hum Genet Jun. 2000;66(6):2020. Greenburg J [corrected to Greenberg J].
EP 20791702.2, Feb. 10, 2023, Extended European Search Report.
Extended European Search Report for Application No. 20791959.8, mailed Jan. 19, 2023.

\* cited by examiner

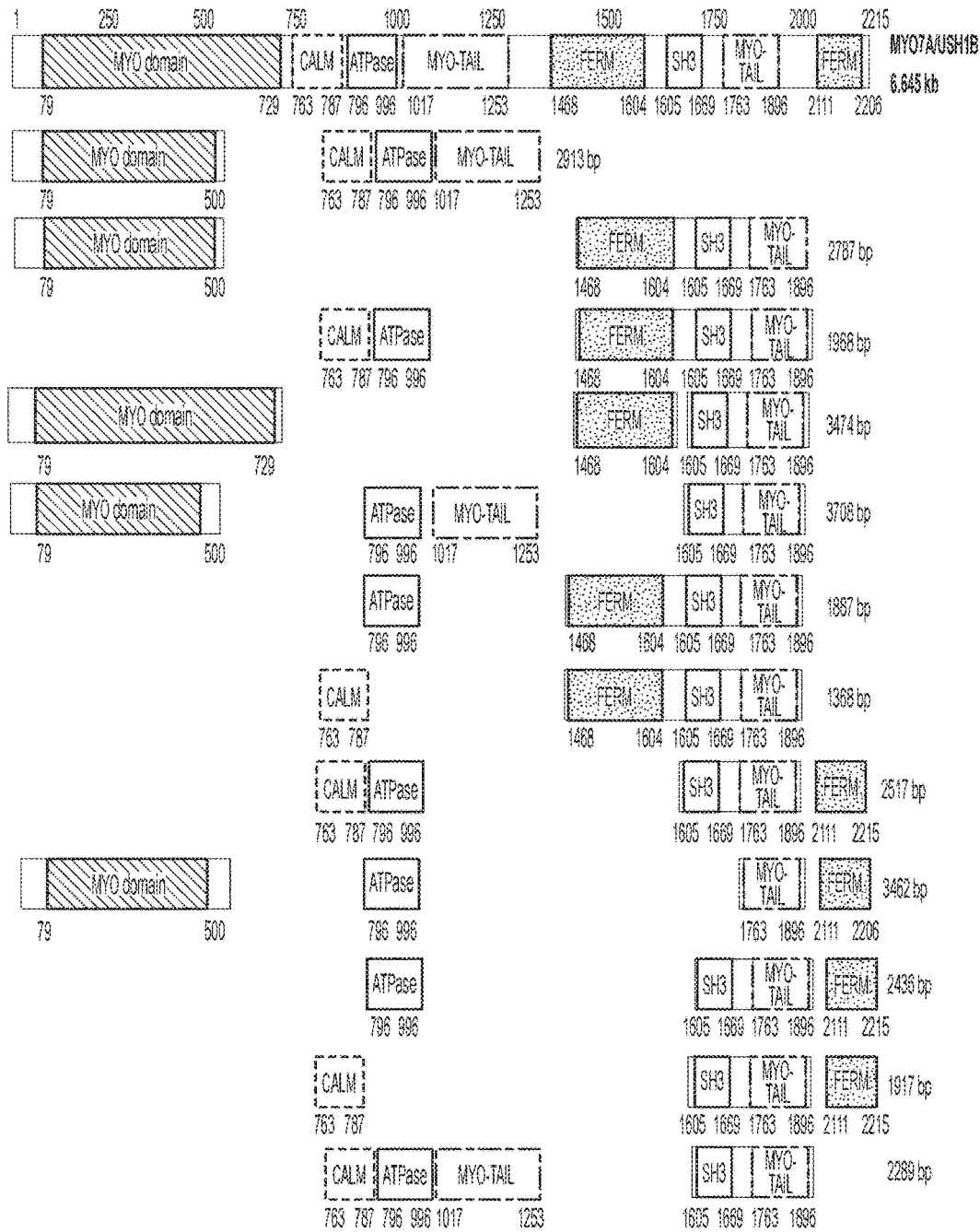

GENE THERAPIES FOR USHER SYNDROME (USH1B)

RELATED APPLICATION

This application is a national stage filing under 35 U.S.C. § 371 of international PCT application PCT/US2020/028489, filed Apr. 16, 2020, which claims priority under 35 U.S.C. § 119(e) to U.S. provisional patent application, U.S. Ser. No. 62/836,414, filed Apr. 19, 2019, the entire contents of each of which are incorporated herein by reference.

BACKGROUND

Usher Syndrome (USH) is a leading cause of deaf-blindness disorder. Patients exhibit severe and progressive retinal degeneration and sensorineural hearing loss. Mutations in the USH1B (MYO7A) gene are associated with >50% of Usher Type I cases. The large size of the USH1B gene (~6.6 kb) has limited the development of successful therapy using conventional Adeno-associated Viral (AAV) vector-mediated gene delivery approaches.

SUMMARY

Aspects of the disclosure relate to compositions and methods useful for delivering minigenes to a subject. Accordingly, the disclosure is based, in part, on isolated nucleic acids and gene therapy vectors, such as viral (e.g., rAAV) vectors, comprising one or more gene fragments encoding a therapeutic gene product, such as a protein or peptide (e.g., a minigene). In some embodiments, the disclosure relates to gene therapy vectors encoding a USH1B protein (e.g., the gene product of USH1B, also referred to as MYO7A) or a portion thereof. In some embodiments, compositions described by the disclosure are useful for treating diseases associated with mutations in the USH1B (MYO7A) gene, for example Usher Syndrome.

Accordingly, in some aspects, the disclosure provides an isolated nucleic acid comprising a transgene encoding a USH1B minigene having the nucleic acid sequence set forth in any one of SEQ ID NOs: 3-14.

In some aspects, the disclosure provides an isolated nucleic acid comprising a transgene having a nucleic acid sequence encoding a USH1B protein, wherein the USHB1 protein comprises an amino acid sequence as set forth in any one of SEQ ID NOs: 15-26.

In some embodiments, a transgene further comprises a promoter operably linked to a USH1B minigene-encoding sequence. In some embodiments, a promoter is a constitutive promoter, inducible promoter, or a tissue-specific promoter. In some embodiments, tissue specific promoter is a photoreceptor-specific promoter. In some embodiments, a photoreceptor-specific promoter is a rhodopsin kinase promoter, such as a human GRK promoter.

In some embodiments, a transgene is flanked by adeno-associated virus (AAV) inverted terminal repeats (ITRs). In some embodiments, at least one of the ITRs flanking a transgene is an AAV2 ITR. In some embodiments the two ITRs flanking the transgene are AAV2 ITRs. In some embodiments, at least one ITR flanking a transgene lacks a terminal resolution site, for example a AITR.

In some aspects, the disclosure provides a vector comprising an isolated nucleic acid as described herein. In some embodiments, a vector is a plasmid DNA, closed-linear DNA, lipid/DNA nanoparticle, or a viral vector. In some embodiments, a viral vector is an adeno-associated virus (AAV) vector, adenoviral (Ad) vector, lentiviral vector, retroviral vector, or Baculovirus vector.

In some aspects, the disclosure provides a host cell comprising an isolated nucleic acid or a vector as described herein. In some embodiments, a cell is a mammalian (human) cell, bacterial cell, yeast cell, or insect cell.

In some aspects, the disclosure provides a recombinant adeno-associated virus (rAAV) comprising: an isolated nucleic acid as described herein; and an AAV capsid protein.

In some embodiments, a capsid protein has a tropism for ocular cells. In some embodiments, a capsid protein is AAV8 capsid protein.

In some embodiments, an rAAV is formulated for delivery to the eye. In some embodiments, an rAAV is formulated for delivery to photoreceptor cells or retinal pigmented epithelium (RPE).

In some aspects, the disclosure provides a composition comprising an isolated nucleic acid or an rAAV as described herein, and a pharmaceutically acceptable excipient.

In some aspects, the disclosure provides a method for delivering a transgene to a cell, the method comprising administering an isolated nucleic acid or an rAAV as described herein to a cell.

In some embodiments, a cell is in a subject. In some embodiments, a subject is a mammalian subject, such as a human subject. In some embodiments, a cell is an eye cell. In some embodiments, an eye cell is a photoreceptor cell or retinal pigmented epithelium (RPE).

In some aspects, the disclosure provides a method for treating Usher Syndrome in a subject in need thereof, the method comprising administering an isolated nucleic acid or an rAAV as described herein to the subject.

In some embodiments, a subject is a mammal. In some embodiments, a subject is a human.

In some embodiments, a subject is characterized by having one or more mutations in a USH1B gene. In some embodiments, a subject has one or more mutations which result in an amino acid substitution selected from G25R, R212C, R302H, A397D, E450Q, and P503L of a USH1B gene.

In some embodiments, administration is via injection. In some embodiments, the injection is subretinal injection or intravitreal injection or suprachoroidal injection.

In some embodiments, administration is topical administration to the eye of a subject.

BRIEF DESCRIPTION OF DRAWINGS

FIG. 1 is a schematic of MiniUSH1B constructs.

DETAILED DESCRIPTION

In some aspects, the disclosure relates to compositions and methods useful for treating certain genetic diseases, for example Usher Syndrome. The disclosure is based, in part, on isolated nucleic acids and gene therapy vectors, such as viral (e.g., rAAV) vectors, comprising one or more gene fragments encoding a therapeutic gene product, such as a MiniUSH1B protein (e.g., the gene product of a USH1B minigene).

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii)

purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.). In some embodiments, an isolated nucleic acid encodes a USH1B protein, such as a MiniUSH1B protein (e.g., a gene product expressed from a USH1B gene or a portion thereof, such as a USH1B minigene).

In humans, the USH1B gene (also referred to as MYO7A) encodes Myosin VIIA protein, which is a member of the unconventional myosin superfamily of proteins. Myosin VIIA has been observed to be involved with movement or linkage of intracellular membranes and organelles to the actin cytoskeleton. Mutations in USH1B gene have been observed to cause Usher Syndrome, which is a combined blindness (e.g., retinal degeneration) and deafness disorder. In some embodiments, a USH1B gene comprises the nucleic acid sequence set forth in NCBI Reference Sequence Accession Number NM 000260.4 (SEQ ID NO: 1). In some embodiments, a USH1B gene encodes a protein having the amino acid sequence set forth in NCBI Reference Sequence Accession Number NP 000251.3 (SEQ ID NO: 2).

As used herein, "minigene" refers to an isolated nucleic acid sequence encoding a recombinant peptide or protein where one or more non-essential elements of the corresponding gene encoding the naturally-occurring peptide or protein have been removed and where the peptide or protein encoded by the minigene retains function of the corresponding naturally-occurring peptide or protein. A "therapeutic minigene" refers to a minigene encoding a peptide or protein useful for treatment of a genetic disease, for example dystrophin, dysferlin, Factor VIII, Amyloid precursor protein (APP), Tyrosinase (Tyr), etc. Minigenes are known in the art and are described, for example by Karpati and Acsadi (1994) *Clin Invest Med* 17(5):499-509; Plantier et al. (2001) *Thromb Haemost.* 86(2):596-603; and Xiao et al. (2007) *World J. Gastroenterol.* 13(2):244-9. In some embodiments, a minigene does not encode the entire amino acid sequence of the naturally-occurring peptide or protein.

In some aspects the disclosure relates to isolated nucleic acids encoding a USH1B minigene. Generally, an isolated nucleic acid encoding a minigene (e.g., a therapeutic minigene, such as a USH1B minigene) is between about 10% and about 99% (e.g., about 10%, about 15%, about 20%, about 25%, about 30%, about 40% about 50%, about 60%, about 70%, about 75%, about 80%, about 90%, about 99%, etc.) truncated with respect to a nucleic acid sequence encoding the corresponding naturally-occurring wild-type protein (e.g., SEQ ID NO: 2). For example, in some embodiments, a minigene encoding a MiniUSH1B protein is between about 61% and truncated (e.g., comprises about 50% of the nucleic acid sequence) compared to a wild-type USH1B gene (e.g., SEQ ID NO: 1). In some embodiments, a USH1B minigene comprises the nucleic acid sequence set forth in any one of SEQ ID NOs: 3-14. In some embodiments, a USH1B minigene encodes a protein (referred to as a MiniUSH1B protein) that comprises an amino acid sequence set forth in any one of SEQ ID NOs: 15-26. In some embodiments, a nucleic acid encoding a USH1B protein (e.g., a MiniUSH1B protein) comprises a start codon (e.g., the nucleic acid sequence ATG) prior to the nucleic acid sequence encoding the USH1B protein. In some embodiments, a nucleic acid sequence encoding a MiniUSHB1 protein is codon-optimized.

An isolated nucleic acid sequence encoding a USH1B protein may be operably linked to a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. A promoter may be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the (3-actin promoter, the phosphoglycerol kinase (PGK) promoter, and the EF1α promoter [Invitrogen]. In some embodiments, a promoter comprises a chicken beta-actin promoter. In some embodiments, a promoter is an enhanced chicken (3-actin promoter. In some embodiments, a promoter is a U6 promoter. In some embodiments, a promoter is a chicken beta-actin (CBA) promoter. In some embodiments, a promoter comprises a rhodopsin kinase promoter, for example a human GRK promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is an eye-specific promoter. Examples of eye-specific promoters include but are not limited to a retinoschisin promoter, K12 promoter, a rhodopsin promoter, a rod-specific promoter, a cone-specific promoter, a rhodopsin kinase promoter, a GRK1 promoter, an interphotoreceptor retinoid-binding protein proximal (IRBP) promoter, and an opsin promoter (e.g., a red opsin promoter, a blue opsin promoter, etc.).

In some embodiments, a promoter is a RNA polymerase III (pol III) promoter. Non-limiting examples of pol III promoters include U6 and H1 promoter sequences. In some embodiments, a promoter is a RNA polymerase II (pol II) promoter. Non-limiting examples of pol II promoters include T7, T3, SP6, RSV, and cytomegalovirus promoter sequences.

Aspects of the disclosure relate to gene therapy vectors comprising an isolated nucleic acid as described herein. A gene therapy vector may be a viral vector (e.g., a lentiviral vector, adenoviral (Ad) vector, an adeno-associated virus vector, etc.), a plasmid DNA, a closed-ended DNA (e.g., ceDNA), lipid/DNA nanoparticle, etc. In some embodiments, a gene therapy vector is a viral vector. In some embodiments, an expression cassette encoding a minigene is flanked by one or more viral replication sequences, for example lentiviral long terminal repeats (LTRs) or adeno-associated virus (AAV) inverted terminal repeats (ITRs).

An isolated nucleic acid described herein may also contain an intron, desirably located between the promoter/enhancer sequence and the transgene. In some embodiments, an intron is a synthetic or artificial (e.g., heterologous) intron. Examples of synthetic introns include an intron sequence derived from SV-40 (referred to as the SV-40 T intron sequence) and intron sequences derived from chicken beta-actin gene. In some embodiments, a transgene described by the disclosure comprises one or more (1, 2, 3, 4, 5, or more) artificial introns. In some embodiments, the one or more artificial introns are positioned between a promoter and a nucleic acid sequence encoding a transgene.

In some embodiments, the rAAV comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the rAAV vector comprises a woodchuck hepatitis virus posttranscriptional regulatory element (WPRE).

In some embodiments, the vector further comprises conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

A polyadenylation sequence generally is inserted following the transgene sequences and optionally before a 3' AAV ITR sequence. A rAAV construct useful in the disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989].

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more proteins (e.g., human USH1B, or a fragment thereof). The transgene may also comprise a region encoding, for example, a miRNA binding site, and/or an expression control sequence (e.g., a poly-A tail).

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, AAV9.hr, AAVrh8, AAVrh10, AAVrh39, AAVrh43, AAV.PHP.B, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, AAV9.hr, AAVrh8, AAVrh10, AAVrh39, AAVrh43, AAV.PHP.B, and variants thereof. In some embodiments, the second AAV ITR is an AAV2 ITR. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ATRS ITR, or AITR). Without wishing to be bound by any particular theory, a rAAV vector comprising an ITR lacking a functional TRS produces a self-complementary rAAV vector, for example as described by McCarthy (2008) Molecular Therapy 16(10):1648-1656.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, AAV10 AAV9.hr, AAVrh8, AAVrh10, AAVrh39, AAVrh43, and AAV.PHP.B. In some embodiments, an AAV capsid protein is of a serotype derived from a non-human primate, for example AAVrh8 serotype. In some embodiments, the AAV capsid protein is of a serotype that has tropism for the eye of a subject, for example an AAV (e.g., AAV5, AAV6, AAV6.2, AAV7, AAV8, AAV9, AAV9.hr, AAVrh8, AAVrh10, AAVrh39, AAVrh43, and AAV.PHP.B) that transduces ocular cells of a subject more efficiently than other vectors. In some embodiments, an AAV capsid protein is of an AAV8 serotype.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component (s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a protein (e.g., a MiniUSH1B protein). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

Delivery

Methods for delivering a transgene to ocular (e.g., photoreceptors, such as rod cells or cone cells, retinal cells, etc.) tissue or the ear of a subject are provided herein. The methods typically involve administering to a subject an effective amount of a rAAV comprising a nucleic acid for expressing a transgene (e.g., a MiniUSH1B protein) in the subject. An "effective amount" of a rAAV is an amount sufficient to infect a sufficient number of cells of a target tissue in a subject. In some embodiments, a target tissue is ocular (e.g., photoreceptor, retinal, etc.) tissue.

An effective amount of a rAAV may be an amount sufficient to have a therapeutic benefit in a subject, e.g., to improve in the subject one or more symptoms of disease, e.g., a symptom of Usher Syndrome (e.g., a disease associated with a deletion or mutation of USH1B gene). Examples of mutations in USH1B gene include G25R, R212C, R302H, A397D, E450Q, and P503L. The effective amount will depend on a variety of factors such as, for example, the species, age, weight, health of the subject, and the ocular tissue to be targeted, and may thus vary among subject and tissue. An effective amount may also depend on the rAAV used.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting an ocular (e.g., photoreceptor, retinal, etc.) tissue by intrastromal administration or subcutaneous injection may require different (e.g., higher or lower) doses, in some cases, than targeting an ocular (e.g., photoreceptor, retinal, etc.) tissue by another method (e.g., systemic administration, topical administration). In some embodiments, intrastromal injection (IS) of rAAV having certain serotypes (e.g., AAV5, AAV6, AAV6.2, AAV7, AAV8, AAV9, AAV9.hr, AAVrh8, AAVrh10, AAVrh39, AAVrh43, and AAV.PHP.B) mediates efficient transduction of ocular (e.g., corneal, photoreceptor, retinal, etc.) cells. Thus, in some embodiments, the injection is intrastromal injection (IS). In some embodiments, the administration is via injection, optionally subretinal injection or intravitreal injection or suprachoroidal injection. In some embodiments, the injection is topical administration (e.g., topical administration to an eye). In some cases, multiple doses of a rAAV are administered.

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject may be by, for example, intraocular injection or topical administration (e.g., eye drops). In some embodiments, the intraocular injection is intrastromal injection, subconjunctival injection, or intravitreal injection. In some embodiments, the injection is not topical administration. Combinations of administration methods (e.g., topical administration and intrastromal injection) can also be used.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline).

Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., ocular tissue, such as photoreceptor, retinal, etc., tissue) and to provide sufficient levels of gene transfer and expression without undue adverse effects. Examples of pharmaceutically acceptable routes of administration include, but are not limited to, direct delivery to the selected organ (e.g., subretinal delivery to the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^9$ rAAV genome copies is effective to target ocular tissue (e.g., corneal tissue). In some embodiments, a dose more concentrated than $10^9$ rAAV genome copies is toxic when administered to the eye of a subject. In some embodiments, an effective amount is produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to ocular tissue (e.g., photoreceptor, retinal, etc., tissue) However, in certain circumstances it may be desirable to separately or in addition deliver the rAAV-based therapeutic constructs via another route, e.g., subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by intravitreal injection or subretinal injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Therapeutic Methods

Aspects of the disclosure relate to methods for delivering a USH1B minigene encoding a MiniUSH1B protein to a cell (e.g., a cell in a subject). In some embodiments, methods described by the disclosure are useful for treating a subject having or suspected of having a disease (e.g., Usher Syndrome). As used herein, Usher Syndrome refers to a disease associated with a deletion or mutation of USH1B gene. A subject having Usher Syndrome may have, in some embodiments, one or more mutations in the USH1B gene that result in an amino acid substitution selected from G25R, R212C, R302H, A397D, E450Q, and P503L (e.g., corresponding to SEQ ID NO: 2). In some embodiments, a subject having Usher Syndrome has lowered or reduced expression or activity of USH1B protein relative to a healthy subject. In some embodiments, a subject having Usher Syndrome is characterized by a level of expression or activity of USH1B protein that is at least 1%, 5%, 10%, 20%, 50%, 75%, or 100% (e.g., no expression of USH1B protein) less than a healthy subject. In some embodiments, a subject having Usher Syndrome is characterized by a level of expression or activity of USH1B that is at least 2-fold, 5-fold, 10-fold, 50-fold, 100-fold, or more less than a healthy subject. A subject may be a human, a mouse, a rat, a pig, a dog, a cat, or a non-human primate.

In some aspects, the disclosure provides a method of promoting expression of USH1B minigene encoding a MiniUSH1B protein in a subject comprising administering the isolated nucleic acids, the rAAVs, or the compositions described herein to a subject having or suspected of having Usher Syndrome. In some embodiments, administering the isolated nucleic acids, the rAAVs, or the compositions described herein to a subject promotes expression of USH1B minigene encoding a MiniUSH1B protein. In some embodiments, administering the isolated nucleic acids, the rAAVs, or the compositions described herein to a subject promotes expression of functional USH1B protein (e.g., a MiniUSH1B protein) by between 2-fold and 100-fold (e.g., 2-fold, 5-fold, 10-fold, 20-fold, 50-fold, 75-fold, 100-fold, etc.) compared to a control subject. In some embodiments, administering the isolated nucleic acids, the rAAVs, or the compositions described herein to a subject promotes expression of functional USH1B protein (e.g., a MiniUSH1B protein) in a subject by between 2-fold and 100-fold (e.g., 2-fold, 5-fold, 10-fold, 20-fold, 50-fold, 75-fold, 100-fold, etc.) compared to a control subject. As used herein a "control" subject may refer to a subject that is not administered the isolated nucleic acids, the rAAVs, or the compositions described herein; or a healthy subject. In some embodiments, a control subject is the same subject that is administered the isolated nucleic acids, the rAAVs, or the compositions described herein (e.g., prior to the administration). In some embodiments, administering the isolated nucleic acids, the rAAVs, or the compositions described to a subject promotes expression of functional USH1B protein (e.g., a MiniUSH1B protein) by 5-fold to 100-fold compared to control (e.g., 5-fold to 10-fold, 10-fold to 15-fold, 10-fold to 20-fold, 15-fold to 25-fold, 20-fold to 30-fold, 25-fold to 35-fold, 30-fold to 40-fold, 35-fold to 45-fold, 40-fold to 60-fold, 50-fold to 75-fold, 60-fold to 80-fold, 75-fold to 100-fold compared to a control).

As used herein, the term "treating" refers to the application or administration of a composition, isolated nucleic acid, vector, or rAAV comprising a USH1B minigene encoding a MiniUSH1B protein to a subject having Usher Syndrome, or a predisposition toward Usher Syndrome, with the purpose to cure, heal, alleviate, relieve, alter, remedy, ameliorate, improve, or affect the disorder, the symptom of the disease, or the predisposition toward Usher Syndrome.

Alleviating Usher Syndrome includes delaying the development or progression of the disease, or reducing disease severity. Alleviating the disease does not necessarily require curative results. As used therein, "delaying" the development of a disease (such as Usher Syndrome) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of Usher Syndrome includes initial onset and/or recurrence.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the disclosure relates to a kit for producing a rAAV, the kit comprising a container housing an isolated nucleic acid described herein. In some embodiments, the kit further comprises instructions for producing the rAAV. In some embodiments, the kit further comprises at least one container housing a recombinant AAV vector, wherein the recombinant AAV vector comprises a transgene.

In some embodiments, the disclosure relates to a kit comprising a container housing a recombinant AAV as described supra. In some embodiments, the kit further comprises a container housing a pharmaceutically acceptable carrier. For example, a kit may comprise one container housing a rAAV and a second container housing a buffer suitable for injection of the rAAV into a subject. In some embodiments, the container is a syringe.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder).

The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1

This example describes identification and production of AAV vectors (and rAAVs) having one or more domains of USH1B (e.g., USH1B minigenes and gene products thereof, "MiniUSH1B") that retain function (e.g., partial USH1B function) in photoreceptors. USH1B is a ciliary protein and regulates cilia growth. Thus, a surrogate screening assay is used to characterize minigenes in the ush1b$^{-/-}$ zebrafish model. MiniUSH1B that show a rescue effect in the fish in in vivo assays are also tested in Ush1b$^{-/-}$ mice. Viral particles are pseudotyped (e.g., AAV2/8) and transgene expression is driven by promoters that predominantly target photoreceptors. MiniUSH1B constructs are delivered into photoreceptors using subretinal injection. FIG. 1 and SEQ ID NOs: 3-14 show embodiments of MiniUSH1B constructs. SEQ ID NOs: 15-26 show embodiments of MiniUSH1B proteins. In some embodiments, a nucleic acid encoding a MiniUSHB1 protein further comprises a start codon (e.g., ATG, AUG) encoding nucleic acid sequence that is upstream (e.g., 5') to the coding sequence of the MiniUSHB1 protein.

Example 2

Zebrafish are injected with mRNA encoding injections with mRNAs encoding USH1B minigene having a nucleic acid sequence constructs set forth in any one of SEQ ID NOs: 3-14 operably linked to a promoter. The effect of degeneration by light damage in the zebrafish on the progression of Usher Syndrome are studied using this assay. Light damage is introduced at three different light intensities and at four different time points using different zebrafish individuals.

USH1B-/- mice are observed over a period of time to determine the accelerated progression timeline of onset Usher Syndrome. Specifically, the expression levels of GFAP (Glial Fibrillary Acidic Protein) and USH1B are determined in four-week old USH1B-/- mice and compared to wild-type mice. GFAP and USH1B expression levels are determined by protein staining methods. The effect of degeneration by light damage in the USH1B−/− mice on the progression of Usher Syndrome are studied using this assay. Light damage is introduced (e.g., into the eye) at three different light intensities and at four different time points using different USH1B−/− mouse individuals.

Example 3

The studies in Example 2 allow for determination of therapeutic intervention using nucleic acids (such as rAAVs) comprising a USH1B minigene having a nucleic acid sequence constructs set forth in any one of SEQ ID NOs: 3-14 operably linked to a promoter. The USH1B minigene constructs are delivered to the USH1B−/− mice (e.g., by delivery into photoreceptor cells using subretinal injection) at varying amounts and on varying timelines. For example, the USH1B minigene constructs are delivered to two- and/or four-week old USH1B−/− mice (e.g., by delivery into photoreceptor cells using subretinal injection) are delivered using single administration or multiple administrations. Wild-type mice (i.e., USH1B+/+ mice) are used as controls. Light damage is introduced (e.g., into the eye) prior to, concurrent with, or following the delivery of the nucleic acids. The light intensity and time duration of the light damage is empirically determined based on Example 2.

GFAP and USH1B expression levels are determined two-, four-, and/or six-weeks after delivery of the nucleic acids. The retinas of the mice are studied two-, four-, and/or six-weeks after light damage or delivery of the nucleic acids. The mice treated with the nucleic acids (such as rAAVs) comprising a USH1B minigene are studied over a longitudinal period (e.g., mice are observed on a bimonthly or monthly basis) after e.g., twelve months of age.

Sequences

In some embodiments, an isolated nucleic acid or vector (e.g., rAAV vector) described by the disclosure comprises or consists of a sequence set forth in any one of SEQ ID NOs: 3-14. In some embodiments, an isolated nucleic acid or vector (e.g., rAAV vector) described by the disclosure comprises or consists of a sequence that is complementary (e.g., the complement of) a sequence set forth in any one of SEQ ID NOs: 3-14. In some embodiments, an isolated nucleic acid or vector (e.g., rAAV vector) described by the disclosure comprises or consists of a sequence that is a reverse complement of a sequence set forth in any one of SEQ ID NOs: 3-14. In some embodiments, an isolated nucleic acid or vector (e.g., rAAV vector) described by the disclosure comprises or consists of a portion of a sequence set forth in any one of SEQ ID NOs: 3-14. A portion may comprise at least 25%, 50%, 60%, 70%, 80%, 90%, 95%, or 99% of a sequence set forth in any one of SEQ ID NOs: 3-14. In some embodiments, a nucleic acid sequence described by the disclosure is a nucleic acid sense strand (e.g., 5' to 3' strand), or in the context of a viral sequences a plus (+) strand. In some embodiments, a nucleic acid sequence described by the disclosure is a nucleic acid antisense strand (e.g., 3' to 5' strand), or in the context of viral sequences a minus (−) strand.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "about" and "substantially" preceding a numerical value represent ±10% of the recited numerical value.

What is claimed is:

1. An isolated nucleic acid comprising a transgene encoding a USH1B minigene having the nucleic acid sequence set forth in any one of SEQ ID NOs: 3-14.

2. The isolated nucleic acid of claim 1, wherein the transgene further comprises a promoter operably linked to the USH1B minigene sequence.

3. The isolated nucleic acid of claim 2, wherein the promoter is a constitutive promoter, inducible promoter, or a tissue-specific promoter.

4. The isolated nucleic acid of claim 1, wherein the transgene is flanked by adeno-associated virus (AAV) inverted terminal repeats (ITRs).

5. The isolated nucleic acid of claim 3, wherein the tissue specific promoter is a photoreceptor-specific promoter.

6. A vector comprising the isolated nucleic acid of claim 1.

7. The vector of claim 6, wherein the vector is a plasmid DNA, closed-linear DNA, lipid/DNA nanoparticle, or a viral vector.

8. The vector of claim 7, wherein the viral vector is an adeno-associated virus (AAV) vector, adenoviral (Ad) vector, lentiviral vector, retroviral vector, or Baculovirus vector.

9. A host cell comprising the isolated nucleic acid of claim 1.

10. A recombinant adeno-associated virus (rAAV) comprising:
(i) the isolated nucleic acid of claim 1; and
(ii) an AAV capsid protein.

11. The rAAV of claim 10, wherein the capsid protein has a tropism for ocular cells.

12. The rAAV of claim 10, wherein the capsid protein is AAV8 capsid protein.

13. The rAAV of claim 10, wherein the rAAV is formulated for delivery to the eye.

14. A composition comprising the isolated nucleic acid of claim 1 and a pharmaceutically acceptable excipient.

15. An isolated nucleic acid comprising a transgene having a nucleic acid sequence encoding a USH1B protein, wherein the USHB1 protein comprises an amino acid sequence as set forth in any one of SEQ ID NOs: 15-26.

* * * * *

SEQUENCE LISTING

```
<160> NUMBER OF SEQ ID NOS: 26

<210> SEQ ID NO 1
<211> LENGTH: 7483
<212> TYPE: DNA
<213> ORGANISM: Artificial Sequence
<220> FEATURE:
<223> OTHER INFORMATION: Synthetic Polynucleotide

<400> SEQUENCE: 1
agtgctggct ggacagctgc tctgggcagg agagagaggg agagacaaga gacacacaca      60
gagagacggc gaggaaggga aagacccaga gggacgccta gaacgagact tggagccaga     120
cagaggaaga ggggacgtgt gtttgcagac tggctgggcc cgtgacccag cttcctgagt     180
cctccgtgca ggtggcagct gtaccaggct ggcaggtcac tgagagtggg cagctgggcc     240
ccagaactgt gcctggccca gtgggcagca ggagctcctg acttgggacc atggtgattc     300
ttcagcaggg ggaccatgtg tggatggacc tgagattggg gcaggagttc gacgtgccca     360
tcggggcggt ggtgaagctc tgcgactctg ggcaggtcca ggtggtggat gatgaagaca     420
atgaacactg gatctctccg cagaacgcaa cgcacatcaa gcctatgcac cccacgtcgg     480
tccacggcgt ggaggacatg atccgcctgg gggacctcaa cgaggcgggc atcttgcgca     540
acctgcttat ccgctaccgg gaccacctca tctacacgta tacgggctcc atcctggtgg     600
ctgtgaaccc ctaccagctg ctctccatct actcgccaga gcacatccgc cagtatacca     660
acaagaagat tggggagatg ccccccccaca tctttgccat tgctgacaac tgctacttca     720
acatgaaacg caacagccga gaccagtgct gcatcatcag tggggaatct ggggccggga     780
agacggagag cacaaagctg atcctgcagt tcctggcagc catcagtggg cagcactcgt     840
ggattgagca gcaggtcttg gaggccaccc ccattctgga agcatttggg aatgccaaga     900
ccatccgcaa tgacaactca agccgtttcg gaaagtacat cgacatccac ttcaacaagc     960
ggggcgccat cgagggcgcg aagattgagc agtacctgct ggaaaagtca cgtgtctgtc    1020
gccaggccct ggatgaaagg aactaccacg tgttctactg catgctggag ggtatgagtg    1080
aggatcagaa gaagaagctg ggcttgggcc aggcctctga ctacaactac ttggccatgg    1140
gtaactgcat aacctgtgag ggccgggtgg acagccagga gtacgccaac atccgctccg    1200
ccatgaaggt gctcatgttc actgacaccg agaactggga gatctcgaag ctcctggctg    1260
ccatcctgca cctgggcaac ctgcagtatg aggcacgcac atttgaaaac ctggatgcct    1320
```

```
gtgaggttct cttctcccca tcgctggcca cagctgcatc cctgcttgag gtgaacccc   1380 cagacctgat gagctgcctg actagccgca ccctcatcac ccgcggggag acggtgtcca   1440
ccccactgag cagggaacag gcactggacg tgcgcgacgc cttcgtaaag gggatctacg   1500
ggcggctgtt cgtgtggatt gtggacaaga tcaacgcagc aatttacaag cctccctccc   1560
aggatgtgaa gaactctcgc aggtccatcg gcctcctgga catctttggg tttgagaact   1620
ttgctgtgaa cagctttgag cagctctgca tcaacttcgc caatgagcac ctgcagcagt   1680
tctttgtgcg gcacgtgttc aagctggagc aggaggaata tgacctggag agcattgact   1740
ggctgcacat cgagttcact gacaaccagg atgccctgga catgattgcc aacaagccca   1800
tgaacatcat ctccctcatc gatgaggaga gcaagttccc caagggcaca gacaccacca   1860
tgttacacaa gctgaactcc cagcacaagc tcaacgccaa ctacatcccc cccaagaaca   1920
accatgagac ccagtttggc atcaaccatt ttgcaggcat cgtctactat gagacccaag   1980
gcttcctgga agaaccgga gacaccctgc atggggacat tatccagctg gtccactcct   2040
ccaggaacaa gttcatcaag cagatcttcc aggccgatgt cgccatgggc gccgagacca   2100
ggaagcgctc gcccacactt agcagccagt tcaagcggtc actggagctg ctgatgcgca   2160
cgctgggtgc ctgccagccc ttctttgtgc gatgcatcaa gcccaatgag ttcaagaagc   2220
ccatgctgtt cgaccggcac ctgtgcgtgc ccagctgcg gtactcagga atgatggaga   2280
ccatccgaat ccgccgagct ggctacccca tccgctacag cttcgtagag tttgtggagc   2340
ggtaccgtgt gctgctgcca ggtgtgaagc cggcctacaa gcagggcgac ctccgcggga   2400
cttgccagcg catggctgag gctgtgctgg gcacccacga tgactggcag ataggcaaaa   2460
ccaagatctt tctgaaggac caccatgaca tgctgctgga agtggagcgg gacaaagcca   2520
tcaccgacag agtcatcctc cttcagaaag tcatccgggg attcaaagac aggtctaact   2580
ttctgaagct gaagaacgct gccacactga tccagaggca ctggcggggt cacaactgta   2640
ggaagaacta cgggctgatg cgtctgggct tcctgcggct gcaggccctg caccgctccc   2700
ggaagctgca ccagcagtac cgcctggccc gccagcgcat catccagttc caggcccgct   2760
gccgcgccta tctggtgcgc aaggccttcc gccaccgcct ctgggctgtg ctcaccgtgc   2820
aggcctatgc ccggggcatg atcgcccgca ggctgcacca acgcctcagg gctgagtatc   2880
tgtggcgcct cgaggctgag aaaatgcggc tggcggagga agagaagctt cggaaggaga   2940
tgagcgccaa gaaggccaag gaggaggccg agcgcaagca tcaggagcgc ctggcccagc   3000
tggctcgtga ggacgctgag cgggagctga aggagaagga ggccgctcgg cggaagaagg   3060
agctcctgga gcagatggaa agggcccgcc atgagcctgt caatcactca gacatggtgg   3120
acaagatgtt tggcttcctg gggacttcag gtggcctgcc aggccaggag ggccaggcac   3180
ctagtggctt tgaggacctg gagcgagggc ggagggagat ggtggaggag gacctggatg   3240
cagccctgcc cctgcctgac gaggatgagg aggacctctc tgagtataaa tttgccaagt   3300
tcgcggccac ctacttccag gggacaacca cgcactccta cacccggcgg ccactcaaac   3360
agccactgct ctaccatgac gacgagggtg accagctggc agccctggcg tctggatca   3420 ccatcctccg cttcatgggg gacctccctg agcccaagta ccacacagcc atgagtgatg   3480
gcagtgagaa gatccctgtg atgaccaaga tttatgagac cctgggcaag aagacgtaca   3540
agagggagct gcaggccctg cagggcgagg cgaggcccca gctccccgag gccagaagaa   3600
agagcagtgt gaggcacaag ctggtgcatt tgactctgaa aaagaagtcc aagctcacag   3660
```

-continued

```
aggaggtgac caagaggctg catgacgggg agtccacagt gcagggcaac agcatgctgg      3720
aggaccggcc cacctccaac ctggagaagc tgcacttcat catcggcaat ggcatcctgc      3780
ggccagcact ccgggacgag atctactgcc agatcagcaa gcagctgacc cacaacccct      3840
ccaagagcag ctatgcccgg ggctggattc tcgtgtctct ctgcgtgggc tgtttcgccc      3900
cctccgagaa gtttgtcaag tacctgcgga acttcatcca cggggcccg cccggctacg       3960
ccccgtactg tgaggagcgc ctgagaagga cctttgtcaa tgggacacgg acacagccgc      4020
ccagctggct ggagctgcag gccaccaagt ccaagaagcc aatcatgttg cccgtgacat      4080
tcatggatgg gaccaccaag accctgctga cggactcggc aaccacggcc aaggagctct      4140
gcaacgcgct ggccgacaag atctctctca aggaccggtt cgggttctcc ctctacattg      4200
ccctgtttga caaggtgtcc tccctgggca gcggcagtga ccacgtcatg gacgccatct      4260
cccagtgcga gcagtacgcc aaggagcagg gcgcccagga gcgcaacgcc ccctggaggc      4320
tcttcttccg caaagaggtc ttcacgcccc ggcacagccc ctccgaggac aacgtggcca      4380
ccaacctcat ctaccagcag gtggtgcgag gagtcaagtt tggggagtac aggtgtgaga      4440
aggaggacga cctggctgag ctggcctccc agcagtactt tgtagactat ggctctgaga      4500
tgatcctgga gcgcctcctg aacctcgtgc ccacctacat ccccgaccgc gagatcacgc      4560
ccctgaagac gctggagaag tgggcccagc tggccatcgc cgcccacaag aaggggattt      4620
atgcccagag gagaactgat gcccagaagg tcaaagagga tgtggtcagt tatgcccgct      4680
tcaagtggcc cttgctcttc tccaggtttt atgaagccta caaattctca ggccccagtc      4740
tccccaagaa cgacgtcatc gtggccgtca actggacggg tgtgtacttt gtggatgagc      4800
aggagcaggt acttctggag ctgtccttcc cagagatcat ggccgtgtcc agcagcaggg      4860
agtgccgtgt ctggctctca ctgggctgct ctgatcttgg ctgtgctgcg cctcactcag      4920
gctgggcagg actgaccccg gcggggccct gttctccgtg ttggtcctgc aggggagcga      4980
aaacgacggc cccagcttc acgctggcca ccatcaaggg ggacgaatac accttcacct      5040
ccagcaatgc tgaggacatt cgtgacctgg tggtcacctt cctagagggg ctccggaaga      5100
gatctaagta tgttgtggcc ctgcaggata accccaaccc cgcaggcgag gagtcaggct      5160
tcctcagctt tgccaaggga gacctcatca tcctggacca tgacacgggc gagcaggtca      5220
tgaactcggg ctgggccaac ggcatcaatg agaggaccaa gcagcgtggg gacttcccca      5280
ccgacagtgt gtacgtcatg cccactgtca ccatgccacc gcgggagatt gtggccctgg      5340
tcaccatgac tcccgatcag aggcaggacg ttgtccggct cttgcagctg cgaacggcgg      5400
agcccgaggt gcgtgccaag ccctacacgc tggaggagtt ttcctatgac tacttcaggc      5460
ccccaccccaa gcacacgctg agccgtgtca tggtgtccaa ggcccgaggc aaggaccggc      5520
tgtggagcca cacgcgggaa ccgctcaagc aggcgctgct caagaagctc ctgggcagtg      5580
aggagctctc gcaggaggcc tgcctggcct tcattgctgt gctcaagtac atgggcgact      5640
acccgtccaa gaggacacgc tccgtcaacg agctcaccga ccagatcttt gagggtcccc      5700
tgaaagccga gccctgaag gacgaggcat atgtgcagat cctgaagcag ctgaccgaca      5760
accacatcag gtacagcgag gagcggggtt gggagctgct ctggctgtgc acgggccttt      5820
tcccacccag caacatcctc ctgccccacg tgcagcgctt cctgcagtcc cgaaagcact      5880
gcccactcgc catcgactgc ctgcaacggc tccagaaagc cctgagaaac gggtcccgga      5940
agtaccctcc gcacctggtg gaggtggagg ccatccagca caagaccacc cagattttcc      6000
acaaagtcta cttccctgat gacactgacg aggccttcga agtggagtcc agcaccaagg      6060
```

```
ccaaggactt ctgccagaac atcgccacca ggctgctcct caagtcctca gagggattca    6120
gcctctttgt caaaattgca gacaaggtcc tcagcgttcc tgagaatgac ttcttctttg    6180
actttgttcg acacttgaca gactggataa agaaagctcg gcccatcaag acggaattg     6240
tgccctcact cacctaccag gtgttcttca tgaagaagct gtggaccacc acggtgccag    6300
ggaaggatcc catggccgat tccatcttcc actattacca ggagttgccc aagtatctcc    6360
gaggctacca caagtgcacg cgggaggagg tgctgcagct gggggcgctg atctacaggg    6420
tcaagttcga ggaggacaag tcctacttcc ccagcatccc caagctgctg cgggagctgg    6480
tgccccagga ccttatccgg caggtctcac ctgatgactg gaagcggtcc atcgtcgcct    6540
acttcaacaa gcacgcaggg aagtccaagg aggaggccaa gctggccttc ctgaagctca    6600
tcttcaagtg gccaccttt ggctcagcct tcttcgaggt gaagcaaact acggagccaa     6660
acttccctga tcctccta attgccatca caagtatgg ggtcagcctc atcgatccca       6720
aaacgaagga tatcctcacc actcatccct tcaccaagat ctccaactgg agcagcggca    6780
acacctactt ccacatcacc attgggaact tggtgcgcgg gagcaaactg ctctgcgaga    6840
cgtcactggg ctacaagatg gatgacctcc tgacttccta cattagccag atgctcacag    6900
ccatgagcaa acagcggggc tccaggagcg gcaagtgaac agtcacgggg aggtgctggt    6960
tccatgcctg ctctcgaggc agcagtgggt tcaggcccat cagctacccc tgcagctggg    7020
gaagacttat gccatcccgg cagcgaggct gggctggcca gccaccactg actataccaa    7080
ctgggcctct gatgttcttc cagtgaggca tctctctggg atgcagaact tccctccatc    7140
cacccctctg gcacctgggt tggtctaatc ctagtttgct gtggccttcc cggttgtgag    7200
agcctgtgat ccttagatgt gtctcctgtt tcagaccagc cccaccatgc aacttccttt    7260
gactttctgt gtaccactgg gatagaggaa tcaagaggac aatctagctc tccatacttt    7320
gaacaaccaa atgtgcattg aatactctga aaccgaaggg actggatctg caggtgggat    7380
gagggagaca gaccactttt ctatattgca gtgtgaatgc tgggcccctg ctcaagtcta    7440
ccctgatcac ctcagggcat aaagcatgtt tcattctctg gcc                      7483
```

<210> SEQ ID NO 2
<211> LENGTH: 2215
<212> TYPE: PRT
<213> ORGANISM: Artificial Sequence
<220> FEATURE:
<223> OTHER INFORMATION: Synthetic Polypeptide

<400> SEQUENCE: 2

```
Met Val Ile Leu Gln Gln Gly Asp His Val Trp Met Asp Leu Arg Leu
1               5                   10                  15

Gly Gln Glu Phe Asp Val Pro Ile Gly Ala Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110
```

```
Ile Tyr Ser Pro Glu His Ile Arg Gln Tyr Thr Asn Lys Lys Ile Gly
            115                 120                 125

Glu Met Pro Pro His Ile Phe Ala Ile Ala Asp Asn Cys Tyr Phe Asn
130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
            195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
            275                 280                 285

Cys Glu Gly Arg Val Asp Ser Gln Glu Tyr Ala Asn Ile Arg Ser Ala
290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
            435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
            515                 520                 525
```

-continued

Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Lys Leu Lys
    755                 760                 765

Asn Ala Ala Thr Leu Ile Gln Arg His Trp Arg Gly His Asn Cys Arg
770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
                805                 810                 815

Ile Ile Gln Phe Gln Ala Arg Cys Arg Ala Tyr Leu Val Arg Lys Ala
            820                 825                 830

Phe Arg His Arg Leu Trp Ala Val Leu Thr Val Gln Ala Tyr Ala Arg
        835                 840                 845

Gly Met Ile Ala Arg Arg Leu His Gln Arg Leu Arg Ala Glu Tyr Leu
    850                 855                 860

Trp Arg Leu Glu Ala Glu Lys Met Arg Leu Ala Glu Glu Glu Lys Leu
865                 870                 875                 880

Arg Lys Glu Met Ser Ala Lys Lys Ala Lys Glu Glu Ala Glu Arg Lys
                885                 890                 895

His Gln Glu Arg Leu Ala Gln Leu Ala Arg Glu Asp Ala Glu Arg Glu
            900                 905                 910

Leu Lys Glu Lys Glu Ala Ala Arg Arg Lys Lys Glu Leu Leu Glu Gln
    915                 920                 925

Met Glu Arg Ala Arg His Glu Pro Val Asn His Ser Asp Met Val Asp
930                 935                 940

Lys Met Phe Gly Phe Leu Gly Thr Ser Gly Gly Leu Pro Gly Gln Glu

```
                 945                 950                 955                 960
            Gly Gln Ala Pro Ser Gly Phe Glu Asp Leu Glu Arg Gly Arg Arg Glu
                             965                 970                 975
            Met Val Glu Glu Asp Leu Asp Ala Ala Leu Pro Leu Pro Asp Glu Asp
                             980                 985                 990
            Glu Glu Asp Leu Ser Glu Tyr Lys Phe Ala Lys Phe Ala Ala Thr Tyr
                             995                 1000                1005
            Phe Gln Gly Thr Thr Thr His Ser Tyr Thr Arg Arg Pro Leu Lys
                1010                    1015                1020
            Gln Pro Leu Leu Tyr His Asp Asp Glu Gly Asp Gln Leu Ala Ala
                1025                    1030                1035
            Leu Ala Val Trp Ile Thr Ile Leu Arg Phe Met Gly Asp Leu Pro
                1040                    1045                1050
            Glu Pro Lys Tyr His Thr Ala Met Ser Asp Gly Ser Glu Lys Ile
                1055                    1060                1065
            Pro Val Met Thr Lys Ile Tyr Glu Thr Leu Gly Lys Lys Thr Tyr
                1070                    1075                1080
            Lys Arg Glu Leu Gln Ala Leu Gln Gly Glu Gly Glu Ala Gln Leu
                1085                    1090                1095
            Pro Glu Gly Gln Lys Lys Ser Ser Val Arg His Lys Leu Val His
                1100                    1105                1110
            Leu Thr Leu Lys Lys Lys Ser Lys Leu Thr Glu Glu Val Thr Lys
                1115                    1120                1125
            Arg Leu His Asp Gly Glu Ser Thr Val Gln Gly Asn Ser Met Leu
                1130                    1135                1140
            Glu Asp Arg Pro Thr Ser Asn Leu Glu Lys Leu His Phe Ile Ile
                1145                    1150                1155
            Gly Asn Gly Ile Leu Arg Pro Ala Leu Arg Asp Glu Ile Tyr Cys
                1160                    1165                1170
            Gln Ile Ser Lys Gln Leu Thr His Asn Pro Ser Lys Ser Ser Tyr
                1175                    1180                1185
            Ala Arg Gly Trp Ile Leu Val Ser Leu Cys Val Gly Cys Phe Ala
                1190                    1195                1200
            Pro Ser Glu Lys Phe Val Lys Tyr Leu Arg Asn Phe Ile His Gly
                1205                    1210                1215
            Gly Pro Pro Gly Tyr Ala Pro Tyr Cys Glu Glu Arg Leu Arg Arg
                1220                    1225                1230
            Thr Phe Val Asn Gly Thr Arg Thr Gln Pro Pro Ser Trp Leu Glu
                1235                    1240                1245
            Leu Gln Ala Thr Lys Ser Lys Lys Pro Ile Met Leu Pro Val Thr
                1250                    1255                1260
            Phe Met Asp Gly Thr Thr Lys Thr Leu Leu Thr Asp Ser Ala Thr
                1265                    1270                1275
            Thr Ala Lys Glu Leu Cys Asn Ala Leu Ala Asp Lys Ile Ser Leu
                1280                    1285                1290
            Lys Asp Arg Phe Gly Phe Ser Leu Tyr Ile Ala Leu Phe Asp Lys
                1295                    1300                1305
            Val Ser Ser Leu Gly Ser Gly Ser Asp His Val Met Asp Ala Ile
                1310                    1315                1320
            Ser Gln Cys Glu Gln Tyr Ala Lys Glu Gln Gly Ala Gln Glu Arg
                1325                    1330                1335
            Asn Ala Pro Trp Arg Leu Phe Phe Arg Lys Glu Val Phe Thr Pro
                1340                    1345                1350
```

-continued

```
Trp His Ser Pro Ser Glu Asp Asn Val Ala Thr Asn Leu Ile Tyr
    1355            1360            1365

Gln Gln Val Val Arg Gly Val Lys Phe Gly Glu Tyr Arg Cys Glu
    1370            1375            1380

Lys Glu Asp Asp Leu Ala Glu Leu Ala Ser Gln Gln Tyr Phe Val
    1385            1390            1395

Asp Tyr Gly Ser Glu Met Ile Leu Glu Arg Leu Leu Asn Leu Val
    1400            1405            1410

Pro Thr Tyr Ile Pro Asp Arg Glu Ile Thr Pro Leu Lys Thr Leu
    1415            1420            1425

Glu Lys Trp Ala Gln Leu Ala Ile Ala Ala His Lys Lys Gly Ile
    1430            1435            1440

Tyr Ala Gln Arg Arg Thr Asp Ala Gln Lys Val Lys Glu Asp Val
    1445            1450            1455

Val Ser Tyr Ala Arg Phe Lys Trp Pro Leu Leu Phe Ser Arg Phe
    1460            1465            1470

Tyr Glu Ala Tyr Lys Phe Ser Gly Pro Ser Leu Pro Lys Asn Asp
    1475            1480            1485

Val Ile Val Ala Val Asn Trp Thr Gly Val Tyr Phe Val Asp Glu
    1490            1495            1500

Gln Glu Gln Val Leu Leu Glu Leu Ser Phe Pro Glu Ile Met Ala
    1505            1510            1515

Val Ser Ser Ser Arg Glu Cys Arg Val Trp Leu Ser Leu Gly Cys
    1520            1525            1530

Ser Asp Leu Gly Cys Ala Ala Pro His Ser Gly Trp Ala Gly Leu
    1535            1540            1545

Thr Pro Ala Gly Pro Cys Ser Pro Cys Trp Ser Cys Arg Gly Ala
    1550            1555            1560

Lys Thr Thr Ala Pro Ser Phe Thr Leu Ala Thr Ile Lys Gly Asp
    1565            1570            1575

Glu Tyr Thr Phe Thr Ser Ser Asn Ala Glu Asp Ile Arg Asp Leu
    1580            1585            1590

Val Val Thr Phe Leu Glu Gly Leu Arg Lys Arg Ser Lys Tyr Val
    1595            1600            1605

Val Ala Leu Gln Asp Asn Pro Asn Pro Ala Gly Glu Glu Ser Gly
    1610            1615            1620

Phe Leu Ser Phe Ala Lys Gly Asp Leu Ile Ile Leu Asp His Asp
    1625            1630            1635

Thr Gly Glu Gln Val Met Asn Ser Gly Trp Ala Asn Gly Ile Asn
    1640            1645            1650

Glu Arg Thr Lys Gln Arg Gly Asp Phe Pro Thr Asp Ser Val Tyr
    1655            1660            1665

Val Met Pro Thr Val Thr Met Pro Pro Arg Glu Ile Val Ala Leu
    1670            1675            1680

Val Thr Met Thr Pro Asp Gln Arg Gln Asp Val Val Arg Leu Leu
    1685            1690            1695

Gln Leu Arg Thr Ala Glu Pro Glu Val Arg Ala Lys Pro Tyr Thr
    1700            1705            1710

Leu Glu Glu Phe Ser Tyr Asp Tyr Phe Arg Pro Pro Pro Lys His
    1715            1720            1725

Thr Leu Ser Arg Val Met Val Ser Lys Ala Arg Gly Lys Asp Arg
    1730            1735            1740
```

Leu Trp Ser His Thr Arg Glu Pro Leu Lys Gln Ala Leu Leu Lys
1745                1750                1755

Lys Leu Leu Gly Ser Glu Glu Leu Ser Gln Glu Ala Cys Leu Ala
1760                1765                1770

Phe Ile Ala Val Leu Lys Tyr Met Gly Asp Tyr Pro Ser Lys Arg
1775                1780                1785

Thr Arg Ser Val Asn Glu Leu Thr Asp Gln Ile Phe Glu Gly Pro
1790                1795                1800

Leu Lys Ala Glu Pro Leu Lys Asp Glu Ala Tyr Val Gln Ile Leu
1805                1810                1815

Lys Gln Leu Thr Asp Asn His Ile Arg Tyr Ser Glu Glu Arg Gly
1820                1825                1830

Trp Glu Leu Leu Trp Leu Cys Thr Gly Leu Phe Pro Pro Ser Asn
1835                1840                1845

Ile Leu Leu Pro His Val Gln Arg Phe Leu Gln Ser Arg Lys His
1850                1855                1860

Cys Pro Leu Ala Ile Asp Cys Leu Gln Arg Leu Gln Lys Ala Leu
1865                1870                1875

Arg Asn Gly Ser Arg Lys Tyr Pro Pro His Leu Val Glu Val Glu
1880                1885                1890

Ala Ile Gln His Lys Thr Thr Gln Ile Phe His Lys Val Tyr Phe
1895                1900                1905

Pro Asp Asp Thr Asp Glu Ala Phe Glu Val Glu Ser Ser Thr Lys
1910                1915                1920

Ala Lys Asp Phe Cys Gln Asn Ile Ala Thr Arg Leu Leu Leu Lys
1925                1930                1935

Ser Ser Glu Gly Phe Ser Leu Phe Val Lys Ile Ala Asp Lys Val
1940                1945                1950

Leu Ser Val Pro Glu Asn Asp Phe Phe Phe Asp Phe Val Arg His
1955                1960                1965

Leu Thr Asp Trp Ile Lys Lys Ala Arg Pro Ile Lys Asp Gly Ile
1970                1975                1980

Val Pro Ser Leu Thr Tyr Gln Val Phe Phe Met Lys Lys Leu Trp
1985                1990                1995

Thr Thr Thr Val Pro Gly Lys Asp Pro Met Ala Asp Ser Ile Phe
2000                2005                2010

His Tyr Tyr Gln Glu Leu Pro Lys Tyr Leu Arg Gly Tyr His Lys
2015                2020                2025

Cys Thr Arg Glu Glu Val Leu Gln Leu Gly Ala Leu Ile Tyr Arg
2030                2035                2040

Val Lys Phe Glu Glu Asp Lys Ser Tyr Phe Pro Ser Ile Pro Lys
2045                2050                2055

Leu Leu Arg Glu Leu Val Pro Gln Asp Leu Ile Arg Gln Val Ser
2060                2065                2070

Pro Asp Asp Trp Lys Arg Ser Ile Val Ala Tyr Phe Asn Lys His
2075                2080                2085

Ala Gly Lys Ser Lys Glu Glu Ala Lys Leu Ala Phe Leu Lys Leu
2090                2095                2100

Ile Phe Lys Trp Pro Thr Phe Gly Ser Ala Phe Phe Glu Val Lys
2105                2110                2115

Gln Thr Thr Glu Pro Asn Phe Pro Glu Ile Leu Leu Ile Ala Ile
2120                2125                2130

Asn Lys Tyr Gly Val Ser Leu Ile Asp Pro Lys Thr Lys Asp Ile

| | | | | | | | | | | |
|---|---|---|---|---|---|---|---|---|---|---|
| | | 2135 | | | 2140 | | | 2145 | | |

Leu Thr Thr His Pro Phe Thr Lys Ile Ser Asn Trp Ser Ser Gly
    2150                2155                2160

Asn Thr Tyr Phe His Ile Thr Ile Gly Asn Leu Val Arg Gly Ser
    2165                2170                2175

Lys Leu Leu Cys Glu Thr Ser Leu Gly Tyr Lys Met Asp Asp Leu
    2180                2185                2190

Leu Thr Ser Tyr Ile Ser Gln Met Leu Thr Ala Met Ser Lys Gln
    2195                2200                2205

Arg Gly Ser Arg Ser Gly Lys
    2210            2215

<210> SEQ ID NO 3
<211> LENGTH: 2913
<212> TYPE: DNA
<213> ORGANISM: Artificial Sequence
<220> FEATURE:
<223> OTHER INFORMATION: Synthetic Polynucleotide

<400> SEQUENCE: 3

| | | |
|---|---|---|
| atggtgattc ttcagcaggg ggaccatgtg tggatggacc tgagattggg gcaggagttc | 60 |
| gacgtgccca tcgggcggt ggtgaagctc tgcgactctg ggcaggtcca ggtggtggat | 120 |
| gatgaagaca tgaacactg gatctctccg cagaacgcaa cgcacatcaa gcctatgcac | 180 |
| cccacgtcgg tccacggcgt ggaggacatg atccgcctgg ggaccctcaa cgaggcgggc | 240 |
| atcttgcgca acctgcttat ccgctaccgg gaccacctca tctacacgta tacgggctcc | 300 |
| atcctggtgg ctgtgaaccc ctaccagctg ctctccatct actcgccaga gcacatccgc | 360 |
| cagtatacca caagaagat tggggagatg ccccccccaca tctttgccat tgctgacaac | 420 |
| tgctacttca acatgaaacg caacagccga gaccagtgct catcatcag tggggaatct | 480 |
| ggggccggga agacggagag cacaaagctg atcctgcagt tcctggcagc catcagtggg | 540 |
| cagcactcgt ggattgagca gcaggtcttg gaggccaccc ccattctgga agcatttggg | 600 |
| aatgccaaga ccatccgcaa tgacaactca agccgtttcg gaaagtacat cgacatccac | 660 |
| ttcaacaagc ggggcgccat cgagggcgcg aagattgagc agtacctgct ggaaaagtca | 720 |
| cgtgtctgtc gccaggccct ggatgaaagg aactaccacg tgttctactg catgctggag | 780 |
| ggtatgagtg aggatcagaa aagaagctg ggcttgggcc aggcctctga ctacaactac | 840 |
| ttggccatgg gtaactgcat aacctgtgag ggccgggtgg acagccagga gtacgccaac | 900 |
| atccgctccg ccatgaaggt gctcatgttc actgacaccg agaactggga gatctcgaag | 960 |
| ctcctggctg ccatcctgca cctgggcaac ctgcagtatg aggcacgcac atttgaaaac | 1020 |
| ctggatgcct gtgaggttct cttctcccca tcgctggcca cagctgcatc cctgcttgag | 1080 |
| gtgaaccccc cagacctgat gagctgcctg actagccgca ccctcatcac ccgcggggag | 1140 |
| acggtgtcca ccccactgag cagggaacag gcactgacgg tgcgcgacgc cttcgtaaag | 1200 |
| gggatctacg gcggctgtt cgtgtggatt gtggacaaga tcaacgcagc aatttacaag | 1260 |
| cctcccctcc aggatgtgaa gaactctcgc aggtccatcg gcctcctgga catctttggg | 1320 |
| tttgagaact tgctgtgaa cagctttgag cagctctgca tcaacttcgc caatgagcac | 1380 |
| ctgcagcagt tctttgtgcg gcacgtgttc aagctggagc aggaggaata tgacctggag | 1440 |
| agcattgact ggctgcacat cgagttcact gacaaccagg atgccctgga catgattgcc | 1500 |
| aggtctaact ttctgaagct gaagaacgct gccacactga tccagaggca ctggcggggt | 1560 |

```
cacaactgta ggaagaacta ccggctgcag gccctgcacc gctcccggaa gctgcaccag    1620
cagtaccgcc tggcccgcca gcgcatcatc cagttccagg cccgctgccg cgcctatctg    1680
gtgcgcaagg ccttccgcca ccgcctctgg gctgtgctca ccgtgcaggc ctatgcccgg    1740
ggcatgatcg cccgcaggct gcaccaacgc ctcagggctg agtatctgtg cgcctcgag     1800 gctgagaaaa tgcggctggc ggaggaagag aagcttcgga aggagatgag cgccaagaag    1860
gccaaggagg aggccgagcg caagcatcag gagcgcctgg cccagctggc tcgtgaggac    1920
gctgagcggg agctgaagga aaggaggcc gctcggcgga agaaggagct cctggagcag     1980
atggaaaggg cccgccatga gcctgtcaat cactcagaca tggtggacaa gatgtttggc    2040
ttcctgggga cttcaggtgg cctgccaggc caggagggcc aggcacctag tggctttgag    2100
gacctggagc gagggcggag ggagatggtg gaggaggacc tggatgcagc cctgcccctg    2160
cctgacgagg atgaggagga ctacacccgg cggccactca acagccact gctctaccat     2220 gacgacgagg gtgaccagct ggcagccctg gcggtctgga tcaccatcct ccgcttcatg    2280
ggggacctcc ctgagcccaa gtaccacaca gccatgagtg atggcagtga aagatccct     2340 gtgatgacca agatttatga gaccctgggc aagaagacgt acaagaggga gctgcaggcc    2400
ctgcagggcg agggcgaggc ccagctcccc gagggccaga agaagagcag tgtgaggcac    2460
aagctggtgc atttgactct gaaaagaag tccaagctca cagaggaggt gaccaagagg     2520
ctgcatgacg gggagtccac agtgcagggc aacagcatgc tggaggaccg gcccacctcc    2580
aacctggaga gctgcactt catcatcggc aatggcatcc tgcggccagc actccgggac     2640
gagatctact gccagatcag caagcagctg acccacaacc cctccaagag cagctatgcc    2700
cggggctgga ttctcgtgtc tctctgcgtg ggctgtttcg ccccctccga agtttgtc      2760 aagtacctgc ggaacttcat ccacgggggc ccgcccggct acgccccgta ctgtgaggag    2820
cgcctgagaa ggacctttgt caatgggaca cggacacagc cgcccagctg gctggagctg    2880
caggccacca gtccaagaa gccaatcatg ttg                                  2913

<210> SEQ ID NO 4
<211> LENGTH: 2787
<212> TYPE: DNA
<213> ORGANISM: Artificial Sequence
<220> FEATURE:
<223> OTHER INFORMATION: Synthetic Polynucleotide

<400> SEQUENCE: 4
atggtgattc ttcagcaggg ggaccatgtg tggatggacc tgagattggg gcaggagttc      60
gacgtgccca tcgggcggt ggtgaagctc tgcgactctg gcaggtcca ggtggtggat       120 gatgaagaca atgaacactg gatctctccg cagaacgcaa cgcacatcaa gcctatgcac     180
cccacgtcgg tccacggcgt ggaggacatg atccgcctgg gggacctcaa cgaggcgggc    240
atcttgcgca acctgcttat ccgctaccgg gaccacctca tctacacgta tacgggctcc    300
atcctggtgg ctgtgaaccc ctaccagctg ctctccatct actcgccaga gcacatccgc    360
cagtatacca acaagaagat tgggagatg ccccccaca tcttgccat gctgacaac         420 tgctacttca acatgaaacg caacagccga gaccagtgct gcatcatcag tggggaatct    480
ggggccggga agacggagag cacaaagctg atcctgcagt tcctggcagc catcagtggg    540
cagcactcgt ggattgagca gcaggtcttg gaggccaccc ccattctgga agcatttggg    600
aatgccaaga ccatccgcaa tgacaactca gccgtttcg gaaagtacat cgacatccac    660
ttcaacaagc ggggcgccat cgagggcgcg aagattgagc agtacctgct ggaaaagtca    720
```

```
cgtgtctgtc gccaggccct ggatgaaagg aactaccacg tgttctactg catgctggag      780
ggtatgagtg aggatcagaa gaagaagctg ggcttgggcc aggcctctga ctacaactac      840
ttggccatgg gtaactgcat aacctgtgag ggccgggtgg acagccagga gtacgccaac      900
atccgctccg ccatgaaggt gctcatgttc actgacaccg agaactggga gatctcgaag      960
ctcctggctg ccatcctgca cctgggcaac ctgcagtatg aggcacgcac atttgaaaac     1020
ctggatgcct gtgaggttct cttctcccca tcgctggcca cagctgcatc cctgcttgag     1080 gtgaacccccc cagacctgat gagctgcctg actagccgca ccctcatcac ccgcggggag     1140
acggtgtcca ccccactgag cagggaacag gcactggacg tgcgcgacgc cttcgtaaag     1200
gggatctacg ggcggctgtt cgtgtggatt gtggacaaga tcaacgcagc aatttacaag     1260
cctccctccc aggatgtgaa gaactctcgc aggtccatcg gcctcctgga catctttggg     1320
tttgagaact tgctgtgaa cagctttgag cagctctgca tcaacttcgc caatgagcac      1380
ctgcagcagt tctttgtgcg gcacgtgttc aagctggagc aggaggaata tgacctggag     1440
agcattgact ggctgcacat cgagttcact gacaaccagg atgccctgga catgattgcc     1500
ttgctcttct ccaggtttta tgaagcctac aaattctcag gccccagtct ccccaagaac     1560
gacgtcatcg tggccgtcaa ctggacgggt gtgtactttg tggatgagca ggagcaggta     1620
cttctggagc tgtccttccc agagatcatg gccgtgtcca gcagcaggga gtgccgtgtc     1680
tggctctcac tgggctgctc tgatcttggc tgtgctgcgc ctcactcagg ctgggcagga     1740
ctgaccccgg cggggccctg ttctccgtgt tggtcctgca ggggagcgaa acgacggcc      1800 cccagcttca cgctggccac catcaagggg gacgaataca ccttcacctc cagcaatgct     1860
gaggacattc gtgacctggt ggtcaccttc ctagaggggc tccggaagag atctaagtat     1920
gttgtggccc tgcaggataa ccccaacccc gcaggcgagg agtcaggctt cctcagcttt     1980
gccaagggag acctcatcat cctgaccat gacacgggcg agcaggtcat gaactcgggc     2040
tgggccaacg gcatcaatga gaggaccaag cagcgtgggg acttccccac cgacagtgtg     2100
tacgtcatgc ccactgtcac catgccaccg cgggagattg tggccctggt caccatgact     2160
cccgatcaga ggcaggacgt tgtccggctc ttgcagctgc gaacggcgga gcccgaggtg     2220
cgtgccaagc cctacacgct ggaggagttt tcctatgact acttcaggcc cccacccaag     2280
cacacgctga gccgtgtcat ggtgtccaag gcccgaggca aggaccggct gtggagccac     2340
acgcgggaac cgctcaagca ggcgctgctc aagaagctcc tgggcagtga ggagctctcg     2400
caggaggcct gcctggcctt cattgctgtg ctcaagtaca tgggcgacta cccgtccaag     2460
aggacacgct ccgtcaacga gctcaccgac cagatctttg agggtcccct gaaagccgag     2520
cccctgaagg acgaggcata tgtgcagatc ctgaagcagc tgaccgacaa ccacatcagg     2580
tacagcgagg agcggggttg ggagctgctc tggctgtgca cgggcctttt cccacccagc     2640
aacatcctcc tgccccacgt gcagcgcttc ctgcagtccc gaaagcactg cccactcgcc     2700
atcgactgcc tgcaacggct ccagaaagcc ctgagaaacg ggtcccggaa gtaccctccg     2760
cacctggtgg aggtggaggc catccag                                         2787
```

<210> SEQ ID NO 5
<211> LENGTH: 1887
<212> TYPE: DNA
<213> ORGANISM: Artificial Sequence
<220> FEATURE:
<223> OTHER INFORMATION: Synthetic Polynucleotide

<400> SEQUENCE: 5

```
cggctgcagg ccctgcaccg ctcccggaag ctgcaccagc agtaccgcct ggcccgccag      60
cgcatcatcc agttccaggc ccgctgccgc gcctatctgg tgcgcaaggc cttccgccac     120
cgcctctggg ctgtgctcac cgtgcaggcc tatgcccggg catgatcgc ccgcaggctg     180
caccaacgcc tcagggctga gtatctgtgg cgcctcgagg ctgagaaaat gcggctggcg     240
gaggaagaga agcttcggaa ggagatgagc gccaagaagg ccaaggagga ggccgagcgc     300
aagcatcagg agcgcctggc ccagctggct cgtgaggacg ctgagcggga gctgaaggag     360
aaggaggccg ctcggcggaa gaaggagctc tggagcaga tggaaagggc ccgccatgag     420
cctgtcaatc actcagacat ggtggacaag atgtttggct tcctggggac ttcaggtggc     480
ctgccaggcc aggagggcca ggcacctagt ggctttgagg acctggagcg agggcggagg     540
gagatggtgg aggaggacct ggatgcagcc ctgcccctgc ctgacgagga tgaggaggac     600
ttgctcttct ccaggtttta tgaagcctac aaattctcag gccccagtct ccccaagaac     660
gacgtcatcg tggccgtcaa ctggacgggt gtgtactttg tggatgagca ggagcaggta     720
cttctggagc tgtccttccc agagatcatg gccgtgtcca gcagcaggga gtgccgtgtc     780
tggctctcac tgggctgctc tgatcttggc tgtgctgcgc ctcactcagg ctgggcagga     840
ctgaccccgg cggggccctg ttctccgtgt tggtcctgca ggggagcgaa aacgacggcc     900
cccagcttca cgctggccac catcaagggg gacgaataca ccttcacctc cagcaatgct     960
gaggacattc gtgacctggt ggtcaccttc ctagagggc tccggaagag atctaagtat    1020
gttgtggccc tgcaggataa ccccaacccc gcaggcgagg agtcaggctt cctcagcttt    1080
gccaagggag acctcatcat cctggaccat gacacgggcg agcaggtcat gaactcgggc    1140
tgggccaacg gcatcaatga gaggaccaag cagcgtgggg acttccccac cgacagtgtg    1200
tacgtcatgc ccactgtcac catgccaccg cgggagattg tggccctggt caccatgact    1260
cccgatcaga ggcaggacgt tgtccggctc ttgcagctgc gaacggcgga gcccgaggtg    1320
cgtgccaagc cctacacgct ggaggagttt tcctatgact acttcaggcc cccacccaag    1380
cacacgctga gccgtgtcat ggtgtccaag gcccgaggca aggaccggct gtggagccac    1440
acgcgggaac cgctcaagca ggcgctgctc aagaagctcc tgggcagtga ggagctctcg    1500
caggaggcct gcctggcctt cattgctgtg ctcaagtaca tgggcgacta cccgtccaag    1560
aggacacgct ccgtcaacga gctcaccgac cagatctttg agggtcccct gaaagccgag    1620
cccctgaagg acgaggcata tgtgcagatc ctgaagcagc tgaccgacaa ccacatcagg    1680
tacagcgagg agcgggggttg ggagctgctc tggctgtgca cgggccttttt cccacccagc    1740
aacatcctcc tgccccacgt gcagcgcttc ctgcagtccc gaaagcactg cccactcgcc    1800
atcgactgcc tgcaacggct ccagaaagcc ctgagaaacg ggtcccggaa gtaccctccg    1860
cacctggtgg aggtggaggc catccag                                         1887
```

<210> SEQ ID NO 6
<211> LENGTH: 3474
<212> TYPE: DNA
<213> ORGANISM: Artificial Sequence
<220> FEATURE:
<223> OTHER INFORMATION: Synthetic Polynucleotide

<400> SEQUENCE: 6

```
atggtgattc ttcagcaggg ggaccatgtg tggatggacc tgagattggg gcaggagttc      60
gacgtgccca tcgggcggt ggtgaagctc tgcgactctg gcaggtcca ggtggtggat     120
```

```
gatgaagaca atgaacactg gatctctccg cagaacgcaa cgcacatcaa gcctatgcac    180
cccacgtcgg tccacggcgt ggaggacatg atccgcctgg ggaccctcaa cgaggcgggc    240
atcttgcgca acctgcttat ccgctaccgg gaccacctca tctacacgta tacgggctcc    300
atcctggtgg ctgtgaaccc ctaccagctg ctctccatct actcgccaga gcacatccgc    360
cagtatacca acaagaagat tggggagatg ccccccaca tctttgccat tgctgacaac    420
tgctacttca acatgaaacg caacagccga gaccagtgct gcatcatcag tggggaatct    480
ggggccggga agacggagag cacaaagctg atcctgcagt tcctggcagc catcagtggg    540
cagcactcgt ggattgagca gcaggtcttg gaggccaccc ccattctgga agcatttggg    600
aatgccaaga ccatccgcaa tgacaactca agccgtttcg gaaagtacat cgacatccac    660
ttcaacaagc ggggcgccat cgagggcgcg aagattgagc agtacctgct ggaaaagtca    720
cgtgtctgtc gccaggccct ggatgaaagg aactaccacg tgttctactg catgctggag    780
ggtatgagtg aggatcagaa gaagaagctg ggcttgggcc aggcctctga ctacaactac    840
ttggccatgg gtaactgcat aacctgtgag ggccgggtgg acagccagga gtacgccaac    900
atccgctccg ccatgaaggt gctcatgttc actgacaccg agaactggga gatctcgaag    960
ctcctggctg ccatcctgca cctgggcaac ctgcagtatg aggcacgcac atttgaaaac   1020
ctggatgcct gtgaggttct cttctcccca tcgctggcca cagctgcatc cctgcttgag   1080 gtgaacccc cagacctgat gagctgcctg actagccgca ccctcatcac ccgcggggag   1140
acggtgtcca ccccactgag cagggaacag gcactggacg tgcgcgacgc cttcgtaaag   1200
gggatctacg ggcggctgtt cgtgtggatt gtggacaaga tcaacgcagc aatttacaag   1260
cctccctccc aggatgtgaa gaactctcgc aggtccatcg gcctcctgga catctttggg   1320
tttgagaact tgctgtgaa cagctttgag cagctctgca tcaacttcgc caatgagcac   1380
ctgcagcagt tctttgtgcg gcacgtgttc aagctggagc aggaggaata tgacctggag   1440
agcattgact ggctgcacat cgagttcact gacaaccagg atgccctgga catgattgcc   1500
aacaagccca tgaacatcat ctccctcatc gatgaggaga gcaagttccc caagggcaca   1560
gacaccacca tgttacacaa gctgaactcc agcacaagc tcaacgccaa ctacatcccc   1620
cccaagaaca accatgagac ccagtttggc atcaaccatt ttgcaggcat cgtctactat   1680
gagacccaag gcttcctgga gaagaaccga gacaccctgc atggggacat tatccagctg   1740
gtccactcct ccaggaacaa gttcatcaag cagatcttcc aggccgatgt cgccatgggc   1800
gccgagacca ggaagcgctc gcccacactt agcagccagt tcaagcggtc actggagctg   1860
ctgatgcgca cgctgggtgc ctgccagccc ttctttgtgc gatgcatcaa gcccaatgag   1920
ttcaagaagc ccatgctgtt cgaccggcac ctgtgcgtgc ccagctgcg gtactcagga   1980 atgatggaga ccatccgaat ccgccgagct ggctacccca tccgctacag cttcgtagag   2040 tttgtgagc ggtaccgtgt gctgctgcca ggtgtgaagc cggcctacaa gcagggcgac   2100
ctccgcggga cttgccagcg catggctgag gctgtgctgg gcacccacga tgactggcag   2160
ataggcaaaa ccaagatctt tctgaagttg ctcttctcca ggttttatga agcctacaaa   2220
ttctcaggcc ccagtctccc caagaacgac gtcatcgtgg ccgtcaactg gacgggtgtg   2280
tactttgtgg atgagcagga gcaggtactt ctggagctgt ccttcccaga gatcatggcc   2340
gtgtccagca gcagggagtg ccgtgtctgg ctctcactgg gctgctctga tcttggctgt   2400
gctgcgcctc actcaggctg ggcaggactg accccggcgg ggccctgttc tccgtgttgg   2460
```

| | |
|---|---|
| tcctgcaggg gagcgaaaac gacggccccc agcttcacgc tggccaccat caaggggac | 2520 |
| gaatacacct tcacctccag caatgctgag gacattcgtg acctggtggt caccttccta | 2580 |
| gaggggctcc ggaagagatc taagtatgtt gtggccctgc aggataaccc caaccccgca | 2640 |
| ggcgaggagt caggcttcct cagctttgcc aagggagacc tcatcatcct ggaccatgac | 2700 |
| acgggcgagc aggtcatgaa ctcgggctgg gccaacggca tcaatgagag gaccaagcag | 2760 |
| cgtggggact cccccaccga cagtgtgtac gtcatgccca ctgtcaccat gccaccgcgg | 2820 |
| gagattgtgg ccctggtcac catgactccc gatcagaggc aggacgttgt ccggctcttg | 2880 |
| cagctgcgaa cggcggagcc cgaggtgcgt gccaagccct acacgctgga ggagttttcc | 2940 |
| tatgactact tcaggccccc acccaagcac acgctgagcc gtgtcatggt gtccaaggcc | 3000 |
| cgaggcaagg accggctgtg gagccacacg cgggaaccgc tcaagcaggc gctgctcaag | 3060 |
| aagctcctgg gcagtgagga gctctcgcag gaggcctgcc tggccttcat tgctgtgctc | 3120 |
| aagtacatgg cgactaccc gtccaagagg acacgctccg tcaacgagct caccgaccag | 3180 |
| atctttgagg gtcccctgaa agccgagccc ctgaaggacg aggcatatgt gcagatcctg | 3240 |
| aagcagctga ccgacaacca catcaggtac agcgaggagc ggggttggga gctgctctgg | 3300 |
| ctgtgcacgg gcctttcc acccagcaac atcctcctgc cccacgtgca cgcttcctg | 3360 |
| cagtcccgaa agcactgccc actcgccatc gactgcctgc aacggctcca gaaagccctg | 3420 |
| agaaacgggt cccggaagta ccctccgcac ctggtggagg tggaggccat ccag | 3474 |

<210> SEQ ID NO 7
<211> LENGTH: 3708
<212> TYPE: DNA
<213> ORGANISM: Artificial Sequence
<220> FEATURE:
<223> OTHER INFORMATION: Synthetic Polynucleotide

<400> SEQUENCE: 7

| | |
|---|---|
| atggtgattc ttcagcaggg ggaccatgtg tggatggacc tgagattggg gcaggagttc | 60 |
| gacgtgccca tcggggcggt ggtgaagctc tgcgactctg ggcaggtcca ggtggtggat | 120 |
| gatgaagaca atgaacactg gatctctccg cagaacgcaa cgcacatcaa gcctatgcac | 180 |
| cccacgtcgg tccacggcgt ggaggacatg atccgcctgg gggacctcaa cgaggcgggc | 240 |
| atcttgcgca acctgcttat ccgctaccgg gaccacctca tctacacgta tcgggctccc | 300 |
| atcctggtgg ctgtgaaccc ctaccagctg ctctccatct actcgccaga gcacatccgc | 360 |
| cagtatacca acaagaagat tggggagatg ccccccaca tctttgccat tgctgacaac | 420 |
| tgctacttca acatgaaacg caacagccga gaccagtgct gcatcatcag tggggaatct | 480 |
| ggggccggga gacggagag cacaaagctg atcctgcagt tcctggcagc catcagtggg | 540 |
| cagcactcgt ggattgagca gcaggtcttg gaggccaccc ccattctgga agcatttggg | 600 |
| aatgccaaga ccatccgcaa tgacaactca agccgtttcg gaaagtacat cgacatccac | 660 |
| ttcaacaagc ggggcgccat cgagggcgcg aagattgagc agtacctgct ggaaaagtca | 720 |
| cgtgtctgtc gccaggccct ggatgaaagg aactaccacg tgttctactg catgctggag | 780 |
| ggtatgagtg aggatcagaa gaagaagctg ggcttgggcc aggcctctga ctacaactac | 840 |
| ttggccatgg gtaactgcat aacctgtgag gccgggtgg acagccagga gtacgccaac | 900 |
| atccgctccg ccatgaaggt gctcatgttc actgacaccg agaactggga gatctcgaag | 960 |
| ctcctggctg ccatcctgca cctgggcaac ctgcagtatg aggcacgcac atttgaaaac | 1020 |
| ctggatgcct gtgaggttct cttctcccca tcgctggcca cagctgcatc cctgcttgag | 1080 |

```
gtgaaccccc cagacctgat gagctgcctg actagccgca ccctcatcac ccgcggggag   1140
acggtgtcca ccccactgag cagggaacag gcactggacg tgcgcgacgc cttcgtaaag   1200
gggatctacg ggcggctgtt cgtgtggatt gtggacaaga tcaacgcagc aatttacaag   1260
cctccctccc aggatgtgaa gaactctcgc aggtccatcg gcctcctgga catctttggg   1320
tttgagaact tgctgtgaa cagctttgag cagctctgca tcaacttcgc caatgagcac   1380
ctgcagcagt tctttgtgcg gcacgtgttc aagctggagc aggaggaata tgacctggag   1440
agcattgact ggctgcacat cgagttcact gacaaccagg atgccctgga catgattgcc   1500
cggctgcagg ccctgcaccg ctcccggaag ctgcaccagc agtaccgcct ggcccgccag   1560
cgcatcatcc agttccaggc ccgctgccgc gcctatctgg tgcgcaaggc cttccgccac   1620
cgcctctggg ctgtgctcac cgtgcaggcc tatgcccggg gcatgatcgc ccgcaggctg   1680
caccaacgcc tcagggctga gtatctgtgg cgcctcgagg ctgagaaaat gcggctggcg   1740
gaggaagaga agcttcggaa ggagatgagc gccaagaagg ccaaggagga ggccgagcgc   1800
aagcatcagg agcgcctggc ccagctggct cgtgaggacg ctgagcggga gctgaaggag   1860
aaggaggccg ctcggcggaa gaaggagctc ctggagcaga tggaaagggc ccgccatgag   1920
cctgtcaatc actcagacat ggtggacaag atgtttggct tcctggggac ttcaggtggc   1980
ctgccaggcc aggagggcca ggcacctagt ggctttgagg acctggagcg agggcggagg   2040
gagatggtgg aggaggacct ggatgcagcc ctgcccctgc ctgacgagga tgaggaggac   2100
tacacccggc ggccactcaa acagccactg ctctaccatg acgacgaggg tgaccagctg   2160
gcagccctgg cggtctggat caccatcctc cgcttcatgg gggacctccc tgagcccaag   2220
taccacacag ccatgagtga tggcagtgag aagatccctg tgatgaccaa gatttatgag   2280
accctgggca agaagacgta caagagggag ctgcaggccc tgcagggcga gggcgaggcc   2340
cagctccccg agggccagaa gaagagcagt gtgaggcaca agctggtgca tttgactctg   2400
aaaaagaagt ccaagctcac agaggaggtg accaagaggc tgcatgacgg ggagtccaca   2460
gtgcagggca acagcatgct ggaggaccgg cccacctcca acctggagaa gctgcacttc   2520
atcatcggca atggcatcct gcggccagca ctccgggacg agatctactg ccagatcagc   2580
aagcagctga cccacaaccc ctccaagagc agctatgccc ggggctggat tctcgtgtct   2640
ctctgcgtgg gctgttttcgc ccctccgag aagtttgtca agtacctgcg gaacttcatc   2700
cacgggggcc cgcccggcta cgccccgtac tgtgaggagc gcctgagaag gacctttgtc   2760
aatgggacac ggacacagcc gcccagctgg ctggagctgc aggccaccaa gtccaagaag   2820
ccaatcatgt tgtctaagta tgttgtggcc ctgcaggata accccaaccc cgcaggcgag   2880
gagtcaggct tcctcagctt tgccaaggga gacctcatca tcctgaccat gacacgggc   2940 gagcaggtca tgaactcggg ctgggccaac ggcatcaatg agaggaccaa gcagcgtggg   3000
gacttcccca ccgacagtgt gtacgtcatg cccactgtca ccatgccacc gcgggagatt   3060
gtggccctgg tcaccatgac tcccgatcag aggcaggacg ttgtccggct cttgcagctg   3120
cgaacggcgg agcccgaggt gcgtgccaag ccctacacgc tggaggagtt ttcctatgac   3180
tacttcaggc ccccaccccaa gcacacgctg agccgtgtca tggtgtccaa ggcccgagcc   3240
aaggaccggc tgtggagcca cacgcgggaa ccgctcaagc aggcgctgct caagaagctc   3300
ctgggcagtg aggagctctc gcaggaggcc tgcctggcct tcattgctgt gctcaagtac   3360
atgggcgact cccgtccaa gaggacacgc tccgtcaacg agctcaccga ccagatcttt   3420
```

-continued

| | |
|---|---|
| gagggtcccc tgaaagccga gccctgaag gacgaggcat atgtgcagat cctgaagcag | 3480 |
| ctgaccgaca accacatcag gtacagcgag gagcggggtt gggagctgct ctggctgtgc | 3540 |
| acgggccttt tcccacccag caacatcctc ctgccccacg tgcagcgctt cctgcagtcc | 3600 |
| cgaaagcact gcccactcgc catcgactgc ctgcaacggc tccagaaagc cctgagaaac | 3660 |
| gggtcccgga agtaccctcc gcacctggtg gaggtggagg ccatccag | 3708 |

<210> SEQ ID NO 8
<211> LENGTH: 1887
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---|
| cggctgcagg ccctgcaccg ctcccggaag ctgcaccagc agtaccgcct ggcccgccag | 60 |
| cgcatcatcc agttccaggc ccgctgccgc gcctatctgg tgcgcaaggc cttccgccac | 120 |
| cgcctctggg ctgtgctcac cgtgcaggcc tatgcccggg gcatgatcgc ccgcaggctg | 180 |
| caccaacgcc tcagggctga gtatctgtgg cgcctcgagg ctgagaaaat gcggctggcg | 240 |
| gaggaagaga agcttcggaa ggagatgagc gccaagaagg ccaaggagga ggccgagcgc | 300 |
| aagcatcagg agcgcctggc ccagctggct cgtgaggacg ctgagcggga gctgaaggag | 360 |
| aaggaggccg ctcggcggaa gaaggagctc ctggagcaga tggaaagggc cgccatgag | 420 |
| cctgtcaatc actcagacat ggtggacaag atgtttggct tcctggggac ttcaggtggc | 480 |
| ctgccaggcc aggagggcca ggcacctagt ggctttgagg acctggagcg agggcggagg | 540 |
| gagatggtgg aggaggacct ggatgcagcc ctgccctgc ctgacgagga tgaggaggac | 600 |
| ttgctcttct ccaggtttta tgaagcctac aaattctcag gccccagtct ccccaagaac | 660 |
| gacgtcatcg tggccgtcaa ctggacgggt gtgtactttg tggatgagca ggagcaggta | 720 |
| cttctggagc tgtccttccc agagatcatg gccgtgtcca gcagggga gtgccgtgtc | 780 |
| tggctctcac tgggctgctc tgatcttggc tgtgctgcgc ctcactcagg ctgggcagga | 840 |
| ctgacccccgg cggggccctg ttctccgtgt tggtcctgca ggggagcgaa acgacggcc | 900 |
| cccagcttca cgctggccac catcaagggg gacgaataca ccttcacctc cagcaatgct | 960 |
| gaggacattc gtgacctggt ggtcaccttc ctagaggggc tccggaagag atctaagtat | 1020 |
| gttgtggccc tgcaggataa ccccaacccc gcaggcgagg agtcaggctt cctcagcttt | 1080 |
| gccaagggag acctcatcat cctggaccat gacacgggcg agcaggtcat gaactcgggc | 1140 |
| tgggccaacg gcatcaatga ggaccaag cagcgtgggg acttccccac cgacagtgtg | 1200 |
| tacgtcatgc ccactgtcac catgccaccg cgggagattg tggccctggt caccatgact | 1260 |
| cccgatcaga ggcaggacgt tgtccggctc ttgcagctgc gaacggcgga gcccgaggtg | 1320 |
| cgtgccaagc cctacacgct ggaggagttt tcctatgact acttcaggcc cccacccaag | 1380 |
| cacacgctga gccgtgtcat ggtgtccaag gcccgaggca aggaccggct gtggagccac | 1440 |
| acgcgggaac cgctcaagca ggcgctgctc aagaagctcc tgggcagtga ggagctctcg | 1500 |
| caggaggcct gcctggcctt cattgctgtg ctcaagtaca tgggcgacta cccgtccaag | 1560 |
| aggacacgct ccgtcaacga gctcaccgac cagatctttg agggtccct gaaagccgag | 1620 |
| cccctgaagg acgaggcata tgtgcagatc ctgaagcagc tgaccgacaa ccacatcagg | 1680 |
| tacagcgagg agcggggttg ggagctgctc tggctgtgca cgggccttt tcccacccagc | 1740 |
| aacatcctcc tgccccacgt gcagcgcttc ctgcagtccc gaaagcactg cccactcgcc | 1800 |

| atcgactgcc tgcaacggct ccagaaagcc ctgagaaacg gtcccggaa gtaccctccg | 1860 |
| cacctggtgg aggtggaggc catccag | 1887 |

<210> SEQ ID NO 9
<211> LENGTH: 1287
<212> TYPE: DNA
<213> ORGANISM: Artificial Sequence
<220> FEATURE:
<223> OTHER INFORMATION: Synthetic Polynucleotide

<400> SEQUENCE: 9

| ttgctcttct ccaggtttta tgaagcctac aaattctcag gccccagtct ccccaagaac | 60 |
| gacgtcatcg tggccgtcaa ctggacgggt gtgtactttg tggatgagca ggagcaggta | 120 |
| cttctggagc tgtccttccc agagatcatg gccgtgtcca gcagggga gtgccgtgtc | 180 |
| tggctctcac tgggctgctc tgatcttggc tgtgctgcgc ctcactcagg ctgggcagga | 240 |
| ctgaccccgg cggggccctg ttctccgtgt tggtcctgca gggagcgaa aacgacggcc | 300 |
| cccagcttca cgctggccac catcaagggg gacgaataca ccttcacctc cagcaatgct | 360 |
| gaggacattc gtgacctggt ggtcaccttc ctagaggggc tccggaagag atctaagtat | 420 |
| gttgtggccc tgcaggataa ccccaacccc gcaggcgagg agtcaggctt cctcagcttt | 480 |
| gccaagggag acctcatcat cctggaccat gacacgggcg agcaggtcat gaactcgggc | 540 |
| tgggccaacg gcatcaatga ggaccaagag cgcgtgggg acttccccac cgacagtgtg | 600 |
| tacgtcatgc ccactgtcac catgccaccg cgggagattg tggccctggt caccatgact | 660 |
| cccgatcaga ggcaggacgt tgtccggctc ttgcagctgc gaacggcgga gcccgaggtg | 720 |
| cgtgccaagc cctacacgct ggaggagttt tcctatgact acttcaggcc cccacccaag | 780 |
| cacacgctga gccgtgtcat ggtgtccaag gcccgaggca aggaccggct gtggagccac | 840 |
| acgcgggaac cgctcaagca ggcgctgctc aagaagctcc tgggcagtga ggagctctcg | 900 |
| caggaggcct gcctggcctt cattgctgtg ctcaagtaca tgggcgacta cccgtccaag | 960 |
| aggacacgct ccgtcaacga gctcaccgac cagatctttg agggtcccct gaaagccgag | 1020 |
| cccctgaagg acgaggcata tgtgcagatc ctgaagcagc tgaccgacaa ccacatcagg | 1080 |
| tacagcgagg agcgggggttg ggagctgctc tggctgtgca cgggccttttt cccacccagc | 1140 |
| aacatcctcc tgccccacgt gcagcgcttc ctgcagtccc gaaagcactg cccactcgcc | 1200 |
| atcgactgcc tgcaacggct ccagaaagcc ctgagaaacg gtcccggaa gtaccctccg | 1260 |
| cacctggtgg aggtggaggc catccag | 1287 |

<210> SEQ ID NO 10
<211> LENGTH: 2517
<212> TYPE: DNA
<213> ORGANISM: Artificial Sequence
<220> FEATURE:
<223> OTHER INFORMATION: Synthetic Polynucleotide

<400> SEQUENCE: 10

| aggtctaact ttctgaagct gaagaacgct gccacactga tccagaggca ctggcggggt | 60 |
| cacaactgta ggaagaacta ccggctgcag gccctgcacc gctcccggaa gctgcaccag | 120 |
| cagtaccgcc tggcccgcca gcgcatcatc cagttccagg cccgctgccg cgcctatctg | 180 |
| gtgcgcaagg ccttccgcca ccgcctctgg gctgtgctca ccgtgcaggc ctatgcccgg | 240 |
| ggcatgatcg cccgcaggct gcaccaacgc ctcagggctg agtatctgtg gcgcctcgag | 300 |

| | |
|---|---|
| gctgagaaaa tgcggctggc ggaggaagag aagcttcgga aggagatgag cgccaagaag | 360 |
| gccaaggagg aggccgagcg caagcatcag gagcgcctgg cccagctggc tcgtgaggac | 420 |
| gctgagcggg agctgaagga gaaggaggcc gctcggcgga agaaggagct cctggagcag | 480 |
| atggaaaggg cccgccatga gcctgtcaat cactcagaca tggtggacaa gatgtttggc | 540 |
| ttcctgggga cttcaggtgg cctgccaggc caggagggcc aggcacctag tggctttgag | 600 |
| gacctggagc gagggcggag ggagatggtg gaggaggacc tggatgcagc cctgcccctg | 660 |
| cctgacgagg atgaggagga ctctaagtat gttgtggccc tgcaggataa ccccaacccc | 720 |
| gcaggcgagg agtcaggctt cctcagcttt gccaagggag acctcatcat cctggaccat | 780 |
| gacacgggcg agcaggtcat gaactcgggc tgggccaacg gcatcaatga ggaggaccaag | 840 |
| cagcgtgggg acttccccac cgacagtgtg tacgtcatgc ccactgtcac catgccaccg | 900 |
| cgggagattg tggccctggt caccatgact cccgatcaga ggcaggacgt tgtccggctc | 960 |
| ttgcagctgc gaacggcgga gcccgaggtg cgtgccaagc cctacacgct ggaggagttt | 1020 |
| tcctatgact acttcaggcc cccacccaag cacacgctga gccgtgtcat ggtgtccaag | 1080 |
| gcccgaggca aggaccggct gtggagccac acgcgggaac cgctcaagca ggcgctgctc | 1140 |
| aagaagctcc tgggcagtga ggagctctcg caggaggcct gcctggcctt cattgctgtg | 1200 |
| ctcaagtaca tgggcgacta cccgtccaag aggacacgct ccgtcaacga gctcaccgac | 1260 |
| cagatctttg agggtcccct gaaagccgag ccctgaagg acgaggcata tgtgcagatc | 1320 |
| ctgaagcagc tgaccgacaa ccacatcagg tacagcgagg agcggggttg ggagctgctc | 1380 |
| tggctgtgca cgggccttt tccacccagc aacatcctcc tgccccacgt gcagcgcttc | 1440 |
| ctgcagtccc gaaagcactg cccactcgcc atcgactgcc tgcaacggct ccagaaagcc | 1500 |
| ctgagaaacg ggtcccggaa gtaccctccg cacctggtgg aggtggaggc catccagcac | 1560 |
| aagaccaccc agattttcca caagtctac ttccctgatg acactgacga ggccttcgaa | 1620 |
| gtggagtcca gcaccaaggc caaggacttc tgccagaaca tcgccaccag gctgctcctc | 1680 |
| aagtcctcag agggattcag cctctttgtc aaaattgcag acaaggtcct cagcgttcct | 1740 |
| gagaatgact tcttctttga ctttgttcga cacttgacag actggataaa gaaagctcgg | 1800 |
| cccatcaagg acggaattgt gccctcactc acctaccagg tgttcttcat gaagaagctg | 1860 |
| tggaccacca cggtgccagg gaaggatccc atggccgatt ccatcttcca ctattaccag | 1920 |
| gagttgccca gtatctccg aggctaccac aagtgcacgc gggaggaggt gctgcagctg | 1980 |
| ggggcgctga tctacagggt caagttcgag gaggacaagt cctacttccc cagcatcccc | 2040 |
| aagctgctgc gggagctggt gccccaggac cttatccggc aggtctcacc tgatgactgg | 2100 |
| aagcggtcca tcgtcgccta cttcaacaag cacgcaggga agtccaagga ggaggccaag | 2160 |
| ctggccttcc tgaagctcat cttcaagtgg cccaccttg gctcagcctt cttcgaggtg | 2220 |
| aagcaaacta cggagccaaa cttccctgag atcctcctaa ttgccatcaa caagtatggg | 2280 |
| gtcagcctca tcgatcccaa aacgaaggat atcctcacca ctcatcccct caccaagatc | 2340 |
| tccaactgga gcagcggcaa cacctacttc cacatcacca ttgggaactt ggtgcgcggg | 2400 |
| agcaaactgc tctgcgagac gtcactgggc tacaagatgg atgacctcct gacttcctac | 2460 |
| attagccaga tgctcacagc catgagcaaa cagcgggggct ccaggagcgg caagtga | 2517 |

<210> SEQ ID NO 11
<211> LENGTH: 3462
<212> TYPE: DNA
<213> ORGANISM: Artificial Sequence
<220> FEATURE:
<223> OTHER INFORMATION: Synthetic Polynucleotide

<400> SEQUENCE: 11

```
atggtgattc ttcagcaggg ggaccatgtg tggatggacc tgagattggg gcaggagttc    60
gacgtgccca tcggggcggt ggtgaagctc tgcgactctg gcaggtcca ggtggtggat    120
gatgaagaca atgaacactg gatctctccg cagaacgcaa cgcacatcaa gcctatgcac   180
cccacgtcgg tccacggcgt ggaggacatg atccgcctgg ggacctcaa cgaggcgggc    240
atcttgcgca acctgcttat ccgctaccgg gaccacctca tctacacgta tacgggctcc    300
atcctggtgc tgtgaaccc ctaccagctg ctctccatct actcgccaga gcacatccgc    360
cagtatacca acaagaagat tggggagatg cccccccaca tctttgccat tgctgacaac   420
tgctacttca acatgaaacg caacagccga gaccagtgct gcatcatcag tggggaatct   480
ggggccggga agacggagag cacaaagctg atcctgcagt cctggcagc catcagtggg    540
cagcactcgt ggattgagca gcaggtcttg gaggccaccc ccattctgga agcatttggg    600
aatgccaaga ccatccgcaa tgacaactca agccgtttcg gaaagtacat cgacatccac    660
ttcaacaagc ggggcgccat cgagggcgcg aagattgagc agtacctgct ggaaaagtca    720
cgtgtctgtc gccaggccct ggatgaaagg aactaccacg tgttctactg catgctggag   780
ggtatgagtg aggatcagaa gaagaagctg ggcttgggcc aggcctctga ctacaactac    840
ttggccatgg gtaactgcat aacctgtgag ggccgggtgg acagccagga gtacgccaac    900
atccgctccg ccatgaaggt gctcatgttc actgacaccg agaactggga gatctcgaag    960
ctcctggctg ccatcctgca cctgggcaac ctgcagtatg aggcacgcac atttgaaaac   1020
ctggatgcct gtgaggttct cttctcccca tcgctggcca cagctgcatc cctgcttgag   1080
gtgaacccc cagacctgat gagctgcctg actagccgca ccctcatcac ccgcggggag   1140
acggtgtcca ccccactgag cagggaacag gcactggacg tgcgcgacgc cttcgtaaag   1200
gggatctacg ggcggctgtt cgtgtggatt gtggacaaga tcaacgcagc aatttacaag   1260
cctccctccc aggatgtgaa gaactctcgc aggtccatcg gcctcctgga catctttggg   1320
tttgagaact tgctgtgaa cagctttgag cagctctgca tcaacttcgc caatgagcac   1380
ctgcagcagt tctttgtgcg gcacgtgttc aagctggagc aggaggaata tgacctggag   1440
agcattgact ggctgcacat cgagttcact gacaaccagg atgccctgga catgattgcc   1500
cggctgcagg ccctgcaccg ctcccggaag ctgcaccagc agtaccgcct ggcccgccag   1560
cgcatcatcc agttccaggc ccgctgccgc gcctatctgg tgcgcaaggc cttccgccac   1620
cgcctctggg ctgtgctcac cgtgcaggcc tatgcccggg gcatgatcgc ccgcaggctg   1680
caccaacgcc tcagggctga gtatctgtgg cgcctcgagg ctgagaaaat gcggctggcg   1740
gaggaagaga agcttcggaa ggagatgagc gccaagaagg ccaaggagga ggccgagcgc   1800
aagcatcagg agcgcctggc ccagctggct cgtgaggacg ctgagcggga gctgaaggag   1860
aaggaggccg ctcggcggaa gaaggagctc ctggagcaga tggaaagggc cgccatgag    1920
cctgtcaatc actcagacat ggtggacaag atgtttggct tcctggggac ttcaggtggc   1980
ctgccaggcc aggagggcca ggcacctagt ggctttgagg acctgagcg agggcggagg   2040
gagatggtgg aggaggacct ggatgcagcc ctgccctgc ctgacgagga tgaggaggac   2100
agtgaggagc tctcgcagga ggcctgcctg gccttcattg ctgtgctcaa gtacatgggc   2160
gactacccgt ccaagaggac acgctccgtc aacgagctca ccgaccagat ctttgagggt   2220
```

| | |
|---|---|
| cccctgaaag ccgagcccct gaaggacgag gcatatgtgc agatcctgaa gcagctgacc | 2280 |
| gacaaccaca tcaggtacag cgaggagcgg ggttgggagc tgctctggct gtgcacgggc | 2340 |
| cttttcccac ccagcaacat cctcctgccc cacgtgcagc gcttcctgca gtcccgaaag | 2400 |
| cactgcccac tcgccatcga ctgcctgcaa cggctccaga aagccctgag aaacgggtcc | 2460 |
| cggaagtacc ctccgcacct ggtggaggtg gaggccatcc agcacaagac cacccagatt | 2520 |
| ttccacaaag tctacttccc tgatgacact gacgaggcct tcgaagtgga gtccagcacc | 2580 |
| aaggccaagg acttctgcca gaacatcgcc accaggctgc tcctcaagtc ctcagaggga | 2640 |
| ttcagcctct tgtcaaaat tgcagacaag gtcctcagcg ttcctgagaa tgacttcttc | 2700 |
| tttgactttg ttcgacactt gacagactgg ataaagaaag ctcggcccat caaggacgga | 2760 |
| attgtgccct cactcaccta ccaggtgttc ttcatgaaga agctgtggac caccacggtg | 2820 |
| ccagggaagg atcccatggc cgattccatc ttccactatt accaggagtt gcccaagtat | 2880 |
| ctccgaggct accacaagtg cacgcgggag gaggtgctgc agctgggggc gctgatctac | 2940 |
| agggtcaagt tcgaggagga caagtcctac ttccccagca tccccaagct gctgcgggag | 3000 |
| ctggtgcccc aggaccttat ccggcaggtc tcacctgatg actggaagcg gtccatcgtc | 3060 |
| gcctacttca acaagcacgc agggaagtcc aaggaggagg ccaagctggc cttcctgaag | 3120 |
| ctcatcttca gtggcccac ctttggctca gccttcttcg aggtgaagca aactacggag | 3180 |
| ccaaacttcc ctgagatcct cctaattgcc atcaacaagt atgggtcag cctcatcgat | 3240 |
| cccaaaacga aggatatcct caccactcat cccttcacca agatctccaa ctggagcagc | 3300 |
| ggcaacaccct acttccacat caccattggg aacttggtgc gcgggagcaa actgctctgc | 3360 |
| gagacgtcac tgggctacaa gatggatgac ctcctgactt cctacattag ccagatgctc | 3420 |
| acagccatga gcaaacagcg gggctccagg agcggcaagt ga | 3462 |

```
<210> SEQ ID NO 12
<211> LENGTH: 2436
<212> TYPE: DNA
<213> ORGANISM: Artificial Sequence
<220> FEATURE:
<223> OTHER INFORMATION: Synthetic Polynucleotide

<400> SEQUENCE: 12
```

| | |
|---|---|
| cggctgcagg ccctgcaccg ctcccggaag ctgcaccagc agtaccgcct ggcccgccag | 60 |
| cgcatcatcc agttccaggc ccgctgccgc gcctatctgg tgcgcaaggc cttccgccac | 120 |
| cgcctctggg ctgtgctcac cgtgcaggcc tatgcccggg gcatgatcgc ccgcaggctg | 180 |
| caccaacgcc tcagggctga gtatctgtgg cgcctcgagg ctgagaaaat gcggctggcg | 240 |
| gaggaagaga agcttcggaa ggagatgagc gccaagaagg ccaaggagga ggccgagcgc | 300 |
| aagcatcagg agcgcctggc ccagctggct cgtgaggacg ctgagcggga gctgaaggag | 360 |
| aaggaggccg ctcggcggaa gaaggagctc tggagcagaa tggaaagggc ccgccatgag | 420 |
| cctgtcaatc actcagacat ggtggacaag atgtttggct tcctggggac ttcaggtggc | 480 |
| ctgccaggcc aggagggcca ggcacctagt ggctttgagg acctggagcg agggcggagg | 540 |
| gagatggtgg aggaggacct ggatgcagcc ctgcccctgc tgacgaggga tgaggaggac | 600 |
| tctaagtatg ttgtggccct gcaggataac cccaaccccg caggcgagga gtcaggcttc | 660 |
| ctcagctttg ccaagggaga cctcatcatc ctggaccatg acacgggcga gcaggtcatg | 720 |
| aactcgggct gggccaacgg catcaatgag aggaccaagc agcgtgggga cttccccacc | 780 |
| gacagtgtgt acgtcatgcc cactgtcacc atgccaccgc gggagattgt ggccctggtc | 840 |

```
accatgactc cgatcagag gcaggacgtt gtccggctct tgcagctgcg aacggcggag    900
cccgaggtgc gtgccaagcc ctacacgctg gaggagtttt cctatgacta cttcaggccc    960
ccacccaagc acacgctgag ccgtgtcatg gtgtccaagg cccgaggcaa ggaccggctg   1020
tggagccaca cgcgggaacc gctcaagcag gcgctgctca agaagctcct gggcagtgag   1080
gagctctcgc aggaggcctg cctggccttc attgctgtgc tcaagtacat gggcgactac   1140
ccgtccaaga ggacacgctc cgtcaacgag ctcaccgacc agatctttga gggtcccctg   1200
aaagccgagc ccctgaagga cgaggcatat gtgcagatcc tgaagcagct gaccgacaac   1260
cacatcaggt acagcgagga gcggggttgg gagctgctct ggctgtgcac gggccttttc   1320
ccacccagca acatcctcct gccccacgtg cagcgcttcc tgcagtcccg aaagcactgc   1380
ccactcgcca tcgactgcct gcaacggctc cagaaagccc tgagaaacgg gtcccggaag   1440
taccctccgc acctggtgga ggtggaggcc atccagcaca gaccaccca gattttccac   1500
aaagtctact ccctgatgaa cactgacgag gccttcgaag tggagtccag caccaaggcc   1560
aaggacttct gccagaacat cgccaccagg ctgctcctca gtcctcaga gggattcagc   1620
ctctttgtca aaattgcaga caaggtcctc agcgttcctg agaatgactt cttctttgac   1680
tttgttcgac acttgacaga ctggataaag aaagctcggc ccatcaagga cggaattgtg   1740
ccctcactca cctaccaggt gttcttcatg aagaagctgt ggaccaccac ggtgccaggg   1800
aaggatccca tggccgattc catcttccac tattaccagg agttgcccaa gtatctccga   1860
ggctaccaca gtgcacgcg ggaggaggtg ctgcagctgg gggcgctgat ctacagggtc   1920
aagttcgagg aggacaagtc ctacttcccc agcatcccca gctgctgcg ggagctggtg   1980
ccccaggacc ttatccggca ggtctcacct gatgactgga gcggtccat cgtcgcctac   2040
ttcaacaagc acgcagggaa gtccaaggag gaggccaagc tggccttcct gaagctcatc   2100
ttcaagtggc ccacctttgg ctcagccttc ttcgaggtga agcaaactac ggagccaaac   2160
ttccctgaga tcctcctaat tgccatcaac aagtatgggg tcagcctcat cgatcccaaa   2220
acgaaggata tcctcaccac tcatcccttc accaagatct ccaactggag cagcggcaac   2280
acctacttcc acatcaccat tgggaacttg gtgcgcggga gcaaactgct ctgcgagacg   2340
tcactgggct acaagatgga tgacctcctg acttcctaca ttagccagat gctcacagcc   2400
atgagcaaac agcggggctc caggagcggc aagtga                             2436
```

<210> SEQ ID NO 13
<211> LENGTH: 1917
<212> TYPE: DNA
<213> ORGANISM: Artificial Sequence
<220> FEATURE:
<223> OTHER INFORMATION: Synthetic Polynucleotide

<400> SEQUENCE: 13

```
aggtctaact ttctgaagct gaagaacgct gccacactga tccagaggca ctggcggggt     60
cacaactgta ggaagaacta ctctaagtat gttgtggccc tgcaggataa ccccaacccc    120
gcaggcgagg agtcaggctt cctcagcttt gccaagggag acctcatcat cctggaccat    180
gacacgggcg agcaggtcat gaactcgggc tgggccaacg gcatcaatga ggaggaccaag   240
cagcgtgggg acttccccac cgacagtgtg tacgtcatgc ccactgtcac catgccaccg    300
cgggagattg tggccctggt caccatgact cccgatcaga ggcaggacgt tgtccggctc    360
ttgcagctgc gaacggcgga gcccgaggtg cgtgccaagc cctacacgct ggaggagttt    420
```

```
tcctatgact acttcaggcc cccacccaag cacacgctga gccgtgtcat ggtgtccaag    480
gcccgaggca aggaccggct gtggagccac acgcgggaac cgctcaagca ggcgctgctc    540
aagaagctcc tgggcagtga ggagctctcg caggaggcct gcctggcctt cattgctgtg    600
ctcaagtaca tgggcgacta cccgtccaag aggacacgct ccgtcaacga gctcaccgac    660
cagatctttg agggtcccct gaaagccgag cccctgaagg acgaggcata tgtgcagatc    720
ctgaagcagc tgaccgacaa ccacatcagg tacagcgagg agcggggttg ggagctgctc    780
tggctgtgca cgggcctttt cccacccagc aacatcctcc tgccccacgt gcagcgcttc    840
ctgcagtccc gaaagcactg cccactcgcc atcgactgcc tgcaacggct ccagaaagcc    900
ctgagaaacg ggtcccggaa gtaccctccg cacctggtgg aggtggaggc catccagcac    960
aagaccaccc agatttttcca caaagtctac ttccctgatg acactgacga ggccttcgaa   1020
gtggagtcca gcaccaaggc caaggacttc tgccagaaca tcgccaccag gctgctcctc   1080
aagtcctcag agggattcag cctctttgtc aaaattgcag acaaggtcct cagcgttcct   1140
gagaatgact tcttctttga ctttgttcga cacttgacag actggataaa gaaagctcgg   1200
cccatcaagg acggaattgt gccctcactc acctaccagg tgttcttcat gaagaagctg   1260
tggaccacca cggtgccagg aaggatcccc atggccgatt ccatcttcca ctattaccag   1320
gagttgccca gtatctccg aggctaccac aagtgcacgc gggaggaggt gctgcagctg   1380
ggggcgctga tctacagggt caagttcgag gaggacaagt cctacttccc cagcatcccc   1440
aagctgctgc gggagctggt gccccaggac cttatccggc aggtctcacc tgatgactgg   1500
aagcggtcca tcgtcgccta cttcaacaag cacgcaggga gtccaaggag ggaggccaag   1560
ctggccttcc tgaagctcat cttcaagtgg cccacctttg gctcagcctt cttcgaggtg   1620
aagcaaacta cggagccaaa cttccctgag atcctcctaa ttgccatcaa caagtatggg   1680
gtcagcctca tcgatcccaa aacgaaggat atcctcacca ctcatccctt caccaagatc   1740
tccaactgga gcagcggcaa cacctacttc cacatcacca tgggaacttt ggtgcgcggg   1800
agcaaactgc tctgcgagac gtcactgggc tacaagatgg atgacctcct gacttcctac   1860
attagccaga tgctcacagc catgagcaaa cagcggggct ccaggagcgg caagtga       1917

<210> SEQ ID NO 14
<211> LENGTH: 2289
<212> TYPE: DNA
<213> ORGANISM: Artificial Sequence
<220> FEATURE:
<223> OTHER INFORMATION: Synthetic Polynucleotide

<400> SEQUENCE: 14
aggtctaact ttctgaagct gaagaacgct gccacactga tccagaggca ctggcggggt     60
cacaactgta ggaagaacta ccggctgcag gccctgcacc gctcccggaa gctgcaccag    120
cagtaccgcc tggcccgcca gcgcatcatc cagttccagg cccgctgccg cgcctatctg    180
gtgcgcaagg ccttccgcca ccgcctctgg gctgtgctca ccgtgcaggc ctatgcccgg    240
ggcatgatcg cccgcaggct gcaccaacgc ctcagggctg agtatctgtg gcgcctcgag    300
gctgagaaaa tgcggctggc ggaggaagag aagcttcgga aggagatgag cgccaagaag    360
gccaaggagg aggccgagcg caagcatcag gagcgcctgg cccagctggc tcgtgaggac    420
gctgagcggg agctgaagga aaggaggcc gtcggcgga agaaggagct cctggagcag    480
atggaaaggg cccgccatga gcctgtcaat cactcagaca tggtggacaa gatgtttggc    540
ttcctgggga cttcaggtgg cctgccaggc caggagggcc aggcacctag tggctttgag    600
```

```
gacctggagc gagggcggag ggagatggtg gaggaggacc tggatgcagc cctgccgctg    660
cctgacgagg atgaggagga ctacacccgg cggccactca acagccact gctctaccat    720 gacgacgagg gtgaccagct ggcagccctg gcggtctgga tcaccatcct ccgcttcatg    780
ggggacctcc ctgagcccaa gtaccacaca gccatgagtg atggcagtga aagatccct    840 gtgatgacca agatttatga accctgggc aagaagacgt acaagaggga gctgcaggcc    900
ctgcagggcg agggcgaggc ccagctcccc gagggccaga gaagagcag tgtgaggcac    960 aagctggtgc atttgactct gaaaagaag tccaagctca cagaggaggt gaccaagagg   1020
ctgcatgacg gggagtccac agtgcagggc aacagcatgc tggaggaccg gcccaccctcc  1080 aacctggaga agctgcactt catcatcggc aatggcatcc tgcggccagc actccgggac  1140
gagatctact gccagatcag caagcagctg acccacaacc cctccaagag cagctatgcc  1200
cggggctgga ttctcgtgtc tctctgcgtg ggctgtttcg ccccctccga agtttgtc   1260 aagtacctgc ggaacttcat ccacgggggc ccgcccggct acgccccgta ctgtgaggag  1320
cgcctgagaa ggacctttgt caatgggaca cggacacagc cgcccagctg gctggagctg  1380
caggccacca gtccaagaa gccaatcatg ttgtctaagt atgttgtggc cctgcaggat  1440
aaccccaacc ccgcaggcga ggagtcaggc ttcctcagct ttgccaaggg agacctcatc  1500
atcctggacc atgacacggg cgagcaggtc atgaactcgg gctgggccaa cggcatcaat  1560
gagaggacca agcagcgtgg ggacttcccc accgacagtg tgtacgtcat gcccactgtc  1620
accatgccac cgcgggagat tgtggccctg gtcaccatga ctcccgatca gaggcaggac  1680
gttgtccggc tcttgcagct gcgaacggcg gagcccgagg tgcgtgccaa gccctacacg  1740
ctggaggagt tttcctatga ctacttcagg ccccccaccca agcacgct gagccgtgtc  1800 atggtgtcca aggcccgagg caaggaccgg ctgtggagcc acacgcggga accgctcaag  1860
caggcgctgc tcaagaagct cctgggcagt gaggagctct cgcaggaggc ctgcctggcc  1920
ttcattgctg tgctcaagta catgggcgac tacccgtcca agaggacacg ctccgtcaac  1980
gagctcaccg accagatctt tgagggtccc ctgaaagccg agcccctgaa ggacgaggca  2040
tatgtgcaga tcctgaagca gctgaccgac aaccacatca ggtacagcga ggagcggggt  2100
tgggagctgc tctggctgtg cacgggcctt ttcccacccca gcaacatcct cctgccccac  2160
gtgcagcgct cctgcagtc ccgaaagcac tgccccactcg ccatcgactg cctgcaacgg  2220
ctccagaaag ccctgagaaa cgggtcccgg aagtaccctc cgcacctggt ggaggtggag  2280
gccatccag                                                         2289
```

<210> SEQ ID NO 15
<211> LENGTH: 971
<212> TYPE: PRT
<213> ORGANISM: Artificial Sequence
<220> FEATURE:
<223> OTHER INFORMATION: Synthetic Polypeptide

<400> SEQUENCE: 15

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
```

```
                50                  55                  60
His Gly Val Glu Asp Met Ile Arg Leu Gly Asp Leu Asn Glu Ala Gly
 65                  70                  75                  80

Ile Leu Arg Asn Leu Leu Ile Arg Tyr Arg Asp His Leu Ile Tyr Thr
                     85                  90                  95

Tyr Thr Gly Ser Ile Leu Val Ala Val Asn Pro Tyr Gln Leu Leu Ser
                100                 105                 110

Ile Tyr Ser Pro Glu His Ile Arg Gln Tyr Thr Asn Lys Lys Ile Gly
                115                 120                 125

Glu Met Pro Pro His Ile Phe Ala Ile Ala Asp Asn Cys Tyr Phe Asn
130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
                180                 185                 190

Thr Pro Ile Leu Glu Ala Phe Gly Asn Ala Lys Thr Ile Arg Asn Asp
                195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
                260                 265                 270

Gly Gln Ala Ser Asp Tyr Asn Tyr Leu Ala Met Gly Asn Cys Ile Thr
                275                 280                 285

Cys Glu Gly Arg Val Asp Ser Gln Glu Tyr Ala Asn Ile Arg Ser Ala
                290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
                340                 345                 350

Ala Thr Ala Ala Ser Leu Leu Glu Val Asn Pro Pro Asp Leu Met Ser
                355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
                420                 425                 430

Ile Gly Leu Leu Asp Ile Phe Gly Phe Glu Asn Phe Ala Val Asn Ser
                435                 440                 445

Phe Glu Gln Leu Cys Ile Asn Phe Ala Asn Glu His Leu Gln Gln Phe
                450                 455                 460

Phe Val Arg His Val Phe Lys Leu Glu Gln Glu Glu Tyr Asp Leu Glu
465                 470                 475                 480
```

```
Ser Ile Asp Trp Leu His Ile Glu Phe Thr Asp Asn Gln Asp Ala Leu
            485                 490                 495

Asp Met Ile Ala Arg Ser Asn Phe Leu Lys Leu Lys Asn Ala Ala Thr
            500                 505                 510

Leu Ile Gln Arg His Trp Arg Gly His Asn Cys Arg Lys Asn Tyr Arg
            515                 520                 525

Leu Gln Ala Leu His Arg Ser Arg Lys Leu His Gln Gln Tyr Arg Leu
            530                 535                 540

Ala Arg Gln Arg Ile Ile Gln Phe Gln Ala Arg Cys Arg Ala Tyr Leu
545                 550                 555                 560

Val Arg Lys Ala Phe Arg His Arg Leu Trp Ala Val Leu Thr Val Gln
            565                 570                 575

Ala Tyr Ala Arg Gly Met Ile Ala Arg Arg Leu His Gln Arg Leu Arg
            580                 585                 590

Ala Glu Tyr Leu Trp Arg Leu Glu Ala Glu Lys Met Arg Leu Ala Glu
            595                 600                 605

Glu Glu Lys Leu Arg Lys Glu Met Ser Ala Lys Lys Ala Lys Glu Glu
            610                 615                 620

Ala Glu Arg Lys His Gln Glu Arg Leu Ala Gln Leu Ala Arg Glu Asp
625                 630                 635                 640

Ala Glu Arg Glu Leu Lys Glu Lys Glu Ala Ala Arg Arg Lys Lys Glu
            645                 650                 655

Leu Leu Glu Gln Met Glu Arg Ala Arg His Glu Pro Val Asn His Ser
            660                 665                 670

Asp Met Val Asp Lys Met Phe Gly Phe Leu Gly Thr Ser Gly Gly Leu
            675                 680                 685

Pro Gly Gln Glu Gly Gln Ala Pro Ser Gly Phe Glu Asp Leu Glu Arg
            690                 695                 700

Gly Arg Arg Glu Met Val Glu Glu Asp Leu Asp Ala Ala Leu Pro Leu
705                 710                 715                 720

Pro Asp Glu Asp Glu Glu Asp Tyr Thr Arg Arg Pro Leu Lys Gln Pro
            725                 730                 735

Leu Leu Tyr His Asp Asp Glu Gly Asp Gln Leu Ala Ala Leu Ala Val
            740                 745                 750

Trp Ile Thr Ile Leu Arg Phe Met Gly Asp Leu Pro Glu Pro Lys Tyr
            755                 760                 765

His Thr Ala Met Ser Asp Gly Ser Glu Lys Ile Pro Val Met Thr Lys
            770                 775                 780

Ile Tyr Glu Thr Leu Gly Lys Lys Thr Tyr Lys Arg Glu Leu Gln Ala
785                 790                 795                 800

Leu Gln Gly Glu Gly Glu Ala Gln Leu Pro Glu Gly Gln Lys Lys Ser
            805                 810                 815

Ser Val Arg His Lys Leu Val His Leu Thr Leu Lys Lys Lys Ser Lys
            820                 825                 830

Leu Thr Glu Glu Val Thr Lys Arg Leu His Asp Gly Glu Ser Thr Val
            835                 840                 845

Gln Gly Asn Ser Met Leu Glu Asp Arg Pro Thr Ser Asn Leu Glu Lys
            850                 855                 860

Leu His Phe Ile Ile Gly Asn Gly Ile Leu Arg Pro Ala Leu Arg Asp
865                 870                 875                 880

Glu Ile Tyr Cys Gln Ile Ser Lys Gln Leu Thr His Asn Pro Ser Lys
            885                 890                 895
```

Ser Ser Tyr Ala Arg Gly Trp Ile Leu Val Ser Leu Cys Val Gly Cys
            900                 905                 910

Phe Ala Pro Ser Glu Lys Phe Val Lys Tyr Leu Arg Asn Phe Ile His
    915                 920                 925

Gly Gly Pro Pro Gly Tyr Ala Pro Tyr Cys Glu Glu Arg Leu Arg Arg
        930                 935                 940

Thr Phe Val Asn Gly Thr Arg Thr Gln Pro Pro Ser Trp Leu Glu Leu
945                 950                 955                 960

Gln Ala Thr Lys Ser Lys Lys Pro Ile Met Leu
                965                 970

<210> SEQ ID NO 16
<211> LENGTH: 929
<212> TYPE: PRT
<213> ORGANISM: Artificial Sequence
<220> FEATURE:
<223> OTHER INFORMATION: Synthetic Polypeptide

<400> SEQUENCE: 16

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

```
Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Leu Leu Phe Ser Arg Phe Tyr Glu Ala Tyr Lys Phe
            500                 505                 510

Ser Gly Pro Ser Leu Pro Lys Asn Asp Val Ile Val Ala Val Asn Trp
        515                 520                 525

Thr Gly Val Tyr Phe Val Asp Glu Gln Glu Gln Val Leu Leu Glu Leu
    530                 535                 540

Ser Phe Pro Glu Ile Met Ala Val Ser Ser Arg Glu Cys Arg Val
545                 550                 555                 560

Trp Leu Ser Leu Gly Cys Ser Asp Leu Gly Cys Ala Ala Pro His Ser
                565                 570                 575

Gly Trp Ala Gly Leu Thr Pro Ala Gly Pro Cys Ser Pro Cys Trp Ser
            580                 585                 590

Cys Arg Gly Ala Lys Thr Thr Ala Pro Ser Phe Thr Leu Ala Thr Ile
        595                 600                 605

Lys Gly Asp Glu Tyr Thr Phe Thr Ser Ser Asn Ala Glu Asp Ile Arg
    610                 615                 620

Asp Leu Val Val Thr Phe Leu Glu Gly Leu Arg Lys Arg Ser Lys Tyr
625                 630                 635                 640

Val Val Ala Leu Gln Asp Asn Pro Asn Pro Ala Gly Glu Glu Ser Gly
                645                 650                 655

Phe Leu Ser Phe Ala Lys Gly Asp Leu Ile Ile Leu Asp His Asp Thr
            660                 665                 670

Gly Glu Gln Val Met Asn Ser Gly Trp Ala Asn Gly Ile Asn Glu Arg
        675                 680                 685

Thr Lys Gln Arg Gly Asp Phe Pro Thr Asp Ser Val Tyr Val Met Pro
    690                 695                 700

Thr Val Thr Met Pro Pro Arg Glu Ile Val Ala Leu Val Thr Met Thr
```

705                 710                 715                 720
        Pro Asp Gln Arg Gln Asp Val Val Arg Leu Leu Gln Leu Arg Thr Ala
                        725                 730                 735

Glu Pro Glu Val Arg Ala Lys Pro Tyr Thr Leu Glu Glu Phe Ser Tyr
                        740                 745                 750

Asp Tyr Phe Arg Pro Pro Lys His Thr Leu Ser Arg Val Met Val
                        755                 760                 765

Ser Lys Ala Arg Gly Lys Asp Arg Leu Trp Ser His Thr Arg Glu Pro
        770                 775                 780

Leu Lys Gln Ala Leu Leu Lys Leu Leu Gly Ser Glu Glu Leu Ser
        785                 790                 795                 800

Gln Glu Ala Cys Leu Ala Phe Ile Ala Val Leu Lys Tyr Met Gly Asp
                        805                 810                 815

Tyr Pro Ser Lys Arg Thr Arg Ser Val Asn Glu Leu Thr Asp Gln Ile
                        820                 825                 830

Phe Glu Gly Pro Leu Lys Ala Glu Pro Leu Lys Asp Glu Ala Tyr Val
                        835                 840                 845

Gln Ile Leu Lys Gln Leu Thr Asp Asn His Ile Arg Tyr Ser Glu Glu
        850                 855                 860

Arg Gly Trp Glu Leu Leu Trp Leu Cys Thr Gly Leu Phe Pro Pro Ser
        865                 870                 875                 880

Asn Ile Leu Leu Pro His Val Gln Arg Phe Leu Gln Ser Arg Lys His
                        885                 890                 895

Cys Pro Leu Ala Ile Asp Cys Leu Gln Arg Leu Gln Lys Ala Leu Arg
                        900                 905                 910

Asn Gly Ser Arg Lys Tyr Pro Pro His Leu Val Glu Val Glu Ala Ile
                        915                 920                 925

Gln

<210> SEQ ID NO 17
<211> LENGTH: 629
<212> TYPE: PRT
<213> ORGANISM: Artificial Sequence
<220> FEATURE:
<223> OTHER INFORMATION: Synthetic Polypeptide

<400> SEQUENCE: 17

Arg Leu Gln Ala Leu His Arg Ser Arg Lys Leu His Gln Gln Tyr Arg
        1               5                   10                  15

Leu Ala Arg Gln Arg Ile Ile Gln Phe Gln Ala Arg Cys Arg Ala Tyr
                        20                  25                  30

Leu Val Arg Lys Ala Phe Arg His Arg Leu Trp Ala Val Leu Thr Val
                        35                  40                  45

Gln Ala Tyr Ala Arg Gly Met Ile Ala Arg Arg Leu His Gln Arg Leu
                        50                  55                  60

Arg Ala Glu Tyr Leu Trp Arg Leu Glu Ala Glu Lys Met Arg Leu Ala
        65                  70                  75                  80

Glu Glu Glu Lys Leu Arg Lys Glu Met Ser Ala Lys Ala Lys Glu
                        85                  90                  95

Glu Ala Glu Arg Lys His Gln Glu Arg Leu Ala Gln Leu Ala Arg Glu
                        100                 105                 110

Asp Ala Glu Arg Glu Leu Lys Glu Lys Glu Ala Ala Arg Arg Lys Lys
                        115                 120                 125

Glu Leu Leu Glu Gln Met Glu Arg Ala Arg His Glu Pro Val Asn His
        130                 135                 140

```
Ser Asp Met Val Asp Lys Met Phe Gly Phe Leu Gly Thr Ser Gly Gly
145                 150                 155                 160

Leu Pro Gly Gln Glu Gly Gln Ala Pro Ser Gly Phe Glu Asp Leu Glu
                165                 170                 175

Arg Gly Arg Arg Glu Met Val Glu Glu Asp Leu Asp Ala Ala Leu Pro
            180                 185                 190

Leu Pro Asp Glu Asp Glu Glu Asp Leu Leu Phe Ser Arg Phe Tyr Glu
            195                 200                 205

Ala Tyr Lys Phe Ser Gly Pro Ser Leu Pro Lys Asn Asp Val Ile Val
        210                 215                 220

Ala Val Asn Trp Thr Gly Val Tyr Phe Val Asp Glu Gln Glu Gln Val
225                 230                 235                 240

Leu Leu Glu Leu Ser Phe Pro Glu Ile Met Ala Val Ser Ser Ser Arg
                245                 250                 255

Glu Cys Arg Val Trp Leu Ser Leu Gly Cys Ser Asp Leu Gly Cys Ala
            260                 265                 270

Ala Pro His Ser Gly Trp Ala Gly Leu Thr Pro Ala Gly Pro Cys Ser
        275                 280                 285

Pro Cys Trp Ser Cys Arg Gly Ala Lys Thr Thr Ala Pro Ser Phe Thr
290                 295                 300

Leu Ala Thr Ile Lys Gly Asp Glu Tyr Thr Phe Thr Ser Ser Asn Ala
305                 310                 315                 320

Glu Asp Ile Arg Asp Leu Val Val Thr Phe Leu Glu Gly Leu Arg Lys
                325                 330                 335

Arg Ser Lys Tyr Val Val Ala Leu Gln Asp Asn Pro Asn Pro Ala Gly
            340                 345                 350

Glu Glu Ser Gly Phe Leu Ser Phe Ala Lys Gly Asp Leu Ile Ile Leu
        355                 360                 365

Asp His Asp Thr Gly Glu Gln Val Met Asn Ser Gly Trp Ala Asn Gly
370                 375                 380

Ile Asn Glu Arg Thr Lys Gln Arg Gly Asp Phe Pro Thr Asp Ser Val
385                 390                 395                 400

Tyr Val Met Pro Thr Val Thr Met Pro Pro Arg Glu Ile Val Ala Leu
                405                 410                 415

Val Thr Met Thr Pro Asp Gln Arg Gln Asp Val Val Arg Leu Leu Gln
            420                 425                 430

Leu Arg Thr Ala Glu Pro Glu Val Arg Ala Lys Pro Tyr Thr Leu Glu
        435                 440                 445

Glu Phe Ser Tyr Asp Tyr Phe Arg Pro Pro Lys His Thr Leu Ser
450                 455                 460

Arg Val Met Val Ser Lys Ala Arg Gly Lys Asp Arg Leu Trp Ser His
465                 470                 475                 480

Thr Arg Glu Pro Leu Lys Gln Ala Leu Leu Lys Lys Leu Leu Gly Ser
                485                 490                 495

Glu Glu Leu Ser Gln Glu Ala Cys Leu Ala Phe Ile Ala Val Leu Lys
            500                 505                 510

Tyr Met Gly Asp Tyr Pro Ser Lys Arg Thr Arg Ser Val Asn Glu Leu
        515                 520                 525

Thr Asp Gln Ile Phe Glu Gly Pro Leu Lys Ala Glu Pro Leu Lys Asp
530                 535                 540

Glu Ala Tyr Val Gln Ile Leu Lys Gln Leu Thr Asp Asn His Ile Arg
545                 550                 555                 560
```

Tyr Ser Glu Glu Arg Gly Trp Glu Leu Leu Trp Leu Cys Thr Gly Leu
                565                 570                 575

Phe Pro Pro Ser Asn Ile Leu Leu Pro His Val Gln Arg Phe Leu Gln
            580                 585                 590

Ser Arg Lys His Cys Pro Leu Ala Ile Asp Cys Leu Gln Arg Leu Gln
        595                 600                 605

Lys Ala Leu Arg Asn Gly Ser Arg Lys Tyr Pro Pro His Leu Val Glu
    610                 615                 620

Val Glu Ala Ile Gln
625

<210> SEQ ID NO 18
<211> LENGTH: 1158
<212> TYPE: PRT
<213> ORGANISM: Artificial Sequence
<220> FEATURE:
<223> OTHER INFORMATION: Synthetic Polypeptide

<400> SEQUENCE: 18

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

```
Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
690                 695                 700

Cys Gln Arg Met Ala Glu Ala Val Leu Gly Thr His Asp Asp Trp Gln
```

```
                705                 710                 715                 720
            Ile Gly Lys Thr Lys Ile Phe Leu Lys Leu Leu Phe Ser Arg Phe Tyr
                                725                 730                 735
            Glu Ala Tyr Lys Phe Ser Gly Pro Ser Leu Pro Lys Asn Asp Val Ile
                                740                 745                 750
            Val Ala Val Asn Trp Thr Gly Val Tyr Phe Val Asp Glu Gln Glu Gln
                                755                 760                 765
            Val Leu Leu Glu Leu Ser Phe Pro Glu Ile Met Ala Val Ser Ser Ser
                770                 775                 780
            Arg Glu Cys Arg Val Trp Leu Ser Leu Gly Cys Ser Asp Leu Gly Cys
            785                 790                 795                 800
            Ala Ala Pro His Ser Gly Trp Ala Gly Leu Thr Pro Ala Gly Pro Cys
                                805                 810                 815
            Ser Pro Cys Trp Ser Cys Arg Gly Ala Lys Thr Thr Ala Pro Ser Phe
                                820                 825                 830
            Thr Leu Ala Thr Ile Lys Gly Asp Glu Tyr Thr Phe Thr Ser Ser Asn
                                835                 840                 845
            Ala Glu Asp Ile Arg Asp Leu Val Val Thr Phe Leu Glu Gly Leu Arg
            850                 855                 860
            Lys Arg Ser Lys Tyr Val Ala Leu Gln Asp Asn Pro Asn Pro Ala
            865                 870                 875                 880
            Gly Glu Glu Ser Gly Phe Leu Ser Phe Ala Lys Gly Asp Leu Ile Ile
                                885                 890                 895
            Leu Asp His Asp Thr Gly Glu Gln Val Met Asn Ser Gly Trp Ala Asn
                                900                 905                 910
            Gly Ile Asn Glu Arg Thr Lys Gln Arg Gly Asp Phe Pro Thr Asp Ser
                                915                 920                 925
            Val Tyr Val Met Pro Thr Val Thr Met Pro Pro Arg Glu Ile Val Ala
                                930                 935                 940
            Leu Val Thr Met Thr Pro Asp Gln Arg Gln Asp Val Val Arg Leu Leu
            945                 950                 955                 960
            Gln Leu Arg Thr Ala Glu Pro Glu Val Arg Ala Lys Pro Tyr Thr Leu
                                965                 970                 975
            Glu Glu Phe Ser Tyr Asp Tyr Phe Arg Pro Pro Pro Lys His Thr Leu
                                980                 985                 990
            Ser Arg Val Met Val Ser Lys Ala  Arg Gly Lys Asp Arg  Leu Trp Ser
                                995                 1000                1005
            His Thr  Arg Glu Pro Leu Lys  Gln Ala Leu Leu Lys  Lys Leu Leu
                1010                1015                1020
            Gly Ser  Glu Glu Leu Ser Gln  Glu Ala Cys Leu Ala  Phe Ile Ala
                1025                1030                1035
            Val Leu  Lys Tyr Met Gly Asp  Tyr Pro Ser Lys Arg  Thr Arg Ser
                1040                1045                1050
            Val Asn  Glu Leu Thr Asp Gln  Ile Phe Glu Gly Pro  Leu Lys Ala
                1055                1060                1065
            Glu Pro  Leu Lys Asp Glu Ala  Tyr Val Gln Ile Leu  Lys Gln Leu
                1070                1075                1080
            Thr Asp  Asn His Ile Arg Tyr  Ser Glu Glu Arg Gly  Trp Glu Leu
                1085                1090                1095
            Leu Trp  Leu Cys Thr Gly Leu  Phe Pro Pro Ser Asn  Ile Leu Leu
                1100                1105                1110
            Pro His  Val Gln Arg Phe Leu  Gln Ser Arg Lys His  Cys Pro Leu
                1115                1120                1125
```

```
Ala Ile Asp Cys Leu Gln Arg  Leu Gln Lys Ala Leu  Arg Asn Gly
    1130            1135             1140

Ser Arg Lys Tyr Pro Pro His  Leu Val Glu Val Glu  Ala Ile Gln
    1145            1150             1155

<210> SEQ ID NO 19
<211> LENGTH: 1236
<212> TYPE: PRT
<213> ORGANISM: Artificial Sequence
<220> FEATURE:
<223> OTHER INFORMATION: Synthetic Polypeptide

<400> SEQUENCE: 19

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335
```

```
Thr Phe Glu Asn Leu Asp Ala Cys Glu Val Leu Phe Ser Pro Ser Leu
                340                 345                 350

Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
                435                 440                 445

Phe Glu Gln Leu Cys Ile Asn Phe Ala Asn Glu His Leu Gln Gln Phe
            450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Arg Leu Gln Ala Leu His Arg Ser Arg Lys Leu His
            500                 505                 510

Gln Gln Tyr Arg Leu Ala Arg Gln Arg Ile Ile Gln Phe Gln Ala Arg
                515                 520                 525

Cys Arg Ala Tyr Leu Val Arg Lys Ala Phe Arg His Arg Leu Trp Ala
            530                 535                 540

Val Leu Thr Val Gln Ala Tyr Ala Arg Gly Met Ile Ala Arg Arg Leu
545                 550                 555                 560

His Gln Arg Leu Arg Ala Glu Tyr Leu Trp Arg Leu Glu Ala Glu Lys
                565                 570                 575

Met Arg Leu Ala Glu Glu Lys Leu Arg Lys Glu Met Ser Ala Lys
            580                 585                 590

Lys Ala Lys Glu Glu Ala Glu Arg Lys His Gln Glu Arg Leu Ala Gln
            595                 600                 605

Leu Ala Arg Glu Asp Ala Glu Arg Glu Leu Lys Glu Lys Glu Ala Ala
            610                 615                 620

Arg Arg Lys Lys Glu Leu Leu Glu Gln Met Glu Arg Ala Arg His Glu
625                 630                 635                 640

Pro Val Asn His Ser Asp Met Val Asp Lys Met Phe Gly Phe Leu Gly
                645                 650                 655

Thr Ser Gly Gly Leu Pro Gly Gln Glu Gly Gln Ala Pro Ser Gly Phe
            660                 665                 670

Glu Asp Leu Glu Arg Gly Arg Arg Glu Met Val Glu Glu Asp Leu Asp
            675                 680                 685

Ala Ala Leu Pro Leu Pro Asp Glu Asp Glu Asp Tyr Thr Arg Arg
            690                 695                 700

Pro Leu Lys Gln Pro Leu Leu Tyr His Asp Asp Glu Gly Asp Gln Leu
705                 710                 715                 720

Ala Ala Leu Ala Val Trp Ile Thr Ile Leu Arg Phe Met Gly Asp Leu
                725                 730                 735

Pro Glu Pro Lys Tyr His Thr Ala Met Ser Asp Gly Ser Glu Lys Ile
            740                 745                 750
```

```
Pro Val Met Thr Lys Ile Tyr Glu Thr Leu Gly Lys Lys Thr Tyr Lys
        755                 760                 765

Arg Glu Leu Gln Ala Leu Gln Gly Gly Gly Ala Gln Leu Pro Glu
    770                 775                 780

Gly Gln Lys Lys Ser Ser Val Arg His Lys Leu Val His Leu Thr Leu
785                 790                 795                 800

Lys Lys Lys Ser Lys Leu Thr Glu Glu Val Thr Lys Arg Leu His Asp
            805                 810                 815

Gly Glu Ser Thr Val Gln Gly Asn Ser Met Leu Glu Asp Arg Pro Thr
        820                 825                 830

Ser Asn Leu Glu Lys Leu His Phe Ile Ile Gly Asn Gly Ile Leu Arg
        835                 840                 845

Pro Ala Leu Arg Asp Glu Ile Tyr Cys Gln Ile Ser Lys Gln Leu Thr
    850                 855                 860

His Asn Pro Ser Lys Ser Ser Tyr Ala Arg Gly Trp Ile Leu Val Ser
865                 870                 875                 880

Leu Cys Val Gly Cys Phe Ala Pro Ser Glu Lys Phe Val Lys Tyr Leu
            885                 890                 895

Arg Asn Phe Ile His Gly Gly Pro Pro Gly Tyr Ala Pro Tyr Cys Glu
                900                 905                 910

Glu Arg Leu Arg Arg Thr Phe Val Asn Gly Thr Arg Thr Gln Pro Pro
        915                 920                 925

Ser Trp Leu Glu Leu Gln Ala Thr Lys Ser Lys Lys Pro Ile Met Leu
        930                 935                 940

Ser Lys Tyr Val Val Ala Leu Gln Asp Asn Pro Asn Pro Ala Gly Glu
945                 950                 955                 960

Glu Ser Gly Phe Leu Ser Phe Ala Lys Gly Asp Leu Ile Ile Leu Asp
            965                 970                 975

His Asp Thr Gly Glu Gln Val Met Asn Ser Gly Trp Ala Asn Gly Ile
            980                 985                 990

Asn Glu Arg Thr Lys Gln Arg Gly Asp Phe Pro Thr Asp Ser Val Tyr
        995                 1000                1005

Val Met Pro Thr Val Thr Met Pro Pro Arg Glu Ile Val Ala Leu
    1010                1015                1020

Val Thr Met Thr Pro Asp Gln Arg Gln Asp Val Val Arg Leu Leu
    1025                1030                1035

Gln Leu Arg Thr Ala Glu Pro Glu Val Arg Ala Lys Pro Tyr Thr
    1040                1045                1050

Leu Glu Glu Phe Ser Tyr Asp Tyr Phe Arg Pro Pro Lys His
    1055                1060                1065

Thr Leu Ser Arg Val Met Val Ser Lys Ala Arg Gly Lys Asp Arg
    1070                1075                1080

Leu Trp Ser His Thr Arg Glu Pro Leu Lys Gln Ala Leu Leu Lys
    1085                1090                1095

Lys Leu Leu Gly Ser Glu Glu Leu Ser Gln Glu Ala Cys Leu Ala
    1100                1105                1110

Phe Ile Ala Val Leu Lys Tyr Met Gly Asp Tyr Pro Ser Lys Arg
    1115                1120                1125

Thr Arg Ser Val Asn Glu Leu Thr Asp Gln Ile Phe Glu Gly Pro
    1130                1135                1140

Leu Lys Ala Glu Pro Leu Lys Asp Glu Ala Tyr Val Gln Ile Leu
    1145                1150                1155

Lys Gln Leu Thr Asp Asn His Ile Arg Tyr Ser Glu Glu Arg Gly
```

```
                1160                1165                1170
Trp Glu Leu Leu Trp Leu Cys Thr Gly Leu Phe Pro Pro Ser Asn
        1175                1180                1185

Ile Leu Leu Pro His Val Gln Arg Phe Leu Gln Ser Arg Lys His
    1190                1195                1200

Cys Pro Leu Ala Ile Asp Cys Leu Gln Arg Leu Gln Lys Ala Leu
        1205                1210                1215

Arg Asn Gly Ser Arg Lys Tyr Pro Pro His Leu Val Glu Val Glu
    1220                1225                1230

Ala Ile Gln
    1235

<210> SEQ ID NO 20
<211> LENGTH: 629
<212> TYPE: PRT
<213> ORGANISM: Artificial Sequence
<220> FEATURE:
<223> OTHER INFORMATION: Synthetic Polypeptide

<400> SEQUENCE: 20

Arg Leu Gln Ala Leu His Arg Ser Arg Lys Leu His Gln Gln Tyr Arg
1               5                   10                  15

Leu Ala Arg Gln Arg Ile Ile Gln Phe Gln Ala Arg Cys Arg Ala Tyr
            20                  25                  30

Leu Val Arg Lys Ala Phe Arg His Arg Leu Trp Ala Val Leu Thr Val
        35                  40                  45

Gln Ala Tyr Ala Arg Gly Met Ile Ala Arg Arg Leu His Gln Arg Leu
    50                  55                  60

Arg Ala Glu Tyr Leu Trp Arg Leu Glu Ala Glu Lys Met Arg Leu Ala
65                  70                  75                  80

Glu Glu Glu Lys Leu Arg Lys Glu Met Ser Ala Lys Lys Ala Lys Glu
                85                  90                  95

Glu Ala Glu Arg Lys His Gln Glu Arg Leu Ala Gln Leu Ala Arg Glu
            100                 105                 110

Asp Ala Glu Arg Glu Leu Lys Glu Lys Glu Ala Ala Arg Arg Lys Lys
        115                 120                 125

Glu Leu Leu Glu Gln Met Glu Arg Ala Arg His Glu Pro Val Asn His
    130                 135                 140

Ser Asp Met Val Asp Lys Met Phe Gly Phe Leu Gly Thr Ser Gly Gly
145                 150                 155                 160

Leu Pro Gly Gln Glu Gly Gln Ala Pro Ser Gly Phe Glu Asp Leu Glu
                165                 170                 175

Arg Gly Arg Arg Glu Met Val Glu Glu Asp Leu Asp Ala Ala Leu Pro
            180                 185                 190

Leu Pro Asp Glu Asp Glu Glu Asp Leu Leu Phe Ser Arg Phe Tyr Glu
        195                 200                 205

Ala Tyr Lys Phe Ser Gly Pro Ser Leu Pro Lys Asn Asp Val Ile Val
    210                 215                 220

Ala Val Asn Trp Thr Gly Val Tyr Phe Val Asp Glu Gln Glu Gln Val
225                 230                 235                 240

Leu Leu Glu Leu Ser Phe Pro Glu Ile Met Ala Val Ser Ser Ser Arg
                245                 250                 255

Glu Cys Arg Val Trp Leu Ser Leu Gly Cys Ser Asp Leu Gly Cys Ala
            260                 265                 270

Ala Pro His Ser Gly Trp Ala Gly Leu Thr Pro Ala Gly Pro Cys Ser
```

```
                275                 280                 285
Pro Cys Trp Ser Cys Arg Gly Ala Lys Thr Thr Ala Pro Ser Phe Thr
290                 295                 300

Leu Ala Thr Ile Lys Gly Asp Glu Tyr Thr Phe Thr Ser Ser Asn Ala
305                 310                 315                 320

Glu Asp Ile Arg Asp Leu Val Val Thr Phe Leu Glu Gly Leu Arg Lys
            325                 330                 335

Arg Ser Lys Tyr Val Val Ala Leu Gln Asp Asn Pro Asn Pro Ala Gly
                340                 345                 350

Glu Glu Ser Gly Phe Leu Ser Phe Ala Lys Gly Asp Leu Ile Ile Leu
            355                 360                 365

Asp His Asp Thr Gly Glu Gln Val Met Asn Ser Gly Trp Ala Asn Gly
370                 375                 380

Ile Asn Glu Arg Thr Lys Gln Arg Gly Asp Phe Pro Thr Asp Ser Val
385                 390                 395                 400

Tyr Val Met Pro Thr Val Thr Met Pro Pro Arg Glu Ile Val Ala Leu
                405                 410                 415

Val Thr Met Thr Pro Asp Gln Arg Gln Asp Val Val Arg Leu Leu Gln
            420                 425                 430

Leu Arg Thr Ala Glu Pro Glu Val Arg Ala Lys Pro Tyr Thr Leu Glu
        435                 440                 445

Glu Phe Ser Tyr Asp Tyr Phe Arg Pro Pro Lys His Thr Leu Ser
    450                 455                 460

Arg Val Met Val Ser Lys Ala Arg Gly Lys Asp Arg Leu Trp Ser His
465                 470                 475                 480

Thr Arg Glu Pro Leu Lys Gln Ala Leu Leu Lys Leu Leu Gly Ser
            485                 490                 495

Glu Glu Leu Ser Gln Glu Ala Cys Leu Ala Phe Ile Ala Val Leu Lys
        500                 505                 510

Tyr Met Gly Asp Tyr Pro Ser Lys Arg Thr Arg Ser Val Asn Glu Leu
    515                 520                 525

Thr Asp Gln Ile Phe Glu Gly Pro Leu Lys Ala Glu Pro Leu Lys Asp
530                 535                 540

Glu Ala Tyr Val Gln Ile Leu Lys Gln Leu Thr Asp Asn His Ile Arg
545                 550                 555                 560

Tyr Ser Glu Glu Arg Gly Trp Glu Leu Leu Trp Leu Cys Thr Gly Leu
            565                 570                 575

Phe Pro Pro Ser Asn Ile Leu Leu Pro His Val Gln Arg Phe Leu Gln
        580                 585                 590

Ser Arg Lys His Cys Pro Leu Ala Ile Asp Cys Leu Gln Arg Leu Gln
    595                 600                 605

Lys Ala Leu Arg Asn Gly Ser Arg Lys Tyr Pro Pro His Leu Val Glu
    610                 615                 620

Val Glu Ala Ile Gln
625

<210> SEQ ID NO 21
<211> LENGTH: 429
<212> TYPE: PRT
<213> ORGANISM: Artificial Sequence
<220> FEATURE:
<223> OTHER INFORMATION: Synthetic Polypeptide

<400> SEQUENCE: 21

Leu Leu Phe Ser Arg Phe Tyr Glu Ala Tyr Lys Phe Ser Gly Pro Ser
```

-continued

```
1               5                   10                  15
Leu Pro Lys Asn Asp Val Ile Ala Val Asn Trp Thr Gly Val Tyr
            20                  25                  30
Phe Val Asp Glu Gln Glu Gln Val Leu Leu Glu Leu Ser Phe Pro Glu
            35                  40                  45
Ile Met Ala Val Ser Ser Arg Glu Cys Arg Val Trp Leu Ser Leu
            50                  55                  60
Gly Cys Ser Asp Leu Gly Cys Ala Ala Pro His Ser Gly Trp Ala Gly
65                  70                  75                  80
Leu Thr Pro Ala Gly Pro Cys Ser Pro Cys Trp Ser Cys Arg Gly Ala
                85                  90                  95
Lys Thr Thr Ala Pro Ser Phe Thr Leu Ala Thr Ile Lys Gly Asp Glu
                100                 105                 110
Tyr Thr Phe Thr Ser Ser Asn Ala Glu Asp Ile Arg Asp Leu Val Val
                115                 120                 125
Thr Phe Leu Glu Gly Leu Arg Lys Arg Ser Lys Tyr Val Val Ala Leu
                130                 135                 140
Gln Asp Asn Pro Asn Pro Ala Gly Glu Glu Ser Gly Phe Leu Ser Phe
145                 150                 155                 160
Ala Lys Gly Asp Leu Ile Ile Leu Asp His Asp Thr Gly Glu Gln Val
                165                 170                 175
Met Asn Ser Gly Trp Ala Asn Gly Ile Asn Glu Arg Thr Lys Gln Arg
                180                 185                 190
Gly Asp Phe Pro Thr Asp Ser Val Tyr Val Met Pro Thr Val Thr Met
                195                 200                 205
Pro Pro Arg Glu Ile Val Ala Leu Val Thr Met Thr Pro Asp Gln Arg
210                 215                 220
Gln Asp Val Val Arg Leu Leu Gln Leu Arg Thr Ala Glu Pro Glu Val
225                 230                 235                 240
Arg Ala Lys Pro Tyr Thr Leu Glu Glu Phe Ser Tyr Asp Tyr Phe Arg
                245                 250                 255
Pro Pro Pro Lys His Thr Leu Ser Arg Val Met Val Ser Lys Ala Arg
                260                 265                 270
Gly Lys Asp Arg Leu Trp Ser His Thr Arg Glu Pro Leu Lys Gln Ala
                275                 280                 285
Leu Leu Lys Lys Leu Leu Gly Ser Glu Glu Leu Ser Gln Glu Ala Cys
                290                 295                 300
Leu Ala Phe Ile Ala Val Leu Lys Tyr Met Gly Asp Tyr Pro Ser Lys
305                 310                 315                 320
Arg Thr Arg Ser Val Asn Glu Leu Thr Asp Gln Ile Phe Glu Gly Pro
                325                 330                 335
Leu Lys Ala Glu Pro Leu Lys Asp Glu Ala Tyr Val Gln Ile Leu Lys
                340                 345                 350
Gln Leu Thr Asp Asn His Ile Arg Tyr Ser Glu Glu Arg Gly Trp Glu
                355                 360                 365
Leu Leu Trp Leu Cys Thr Gly Leu Phe Pro Pro Ser Asn Ile Leu Leu
                370                 375                 380
Pro His Val Gln Arg Phe Leu Gln Ser Arg Lys His Cys Pro Leu Ala
385                 390                 395                 400
Ile Asp Cys Leu Gln Arg Leu Gln Lys Ala Leu Arg Asn Gly Ser Arg
                405                 410                 415
Lys Tyr Pro Pro His Leu Val Glu Val Glu Ala Ile Gln
                420                 425
```

<210> SEQ ID NO 22
<211> LENGTH: 838
<212> TYPE: PRT
<213> ORGANISM: Artificial Sequence
<220> FEATURE:
<223> OTHER INFORMATION: Synthetic Polypeptide

<400> SEQUENCE: 22

```
Arg Ser Asn Phe Leu Lys Leu Lys Asn Ala Ala Thr Leu Ile Gln Arg
1               5                   10                  15

His Trp Arg Gly His Asn Cys Arg Lys Asn Tyr Arg Leu Gln Ala Leu
            20                  25                  30

His Arg Ser Arg Lys Leu His Gln Gln Tyr Arg Leu Ala Arg Gln Arg
        35                  40                  45

Ile Ile Gln Phe Gln Ala Arg Cys Arg Ala Tyr Leu Val Arg Lys Ala
    50                  55                  60

Phe Arg His Arg Leu Trp Ala Val Leu Thr Val Gln Ala Tyr Ala Arg
65                  70                  75                  80

Gly Met Ile Ala Arg Arg Leu His Gln Arg Leu Arg Ala Glu Tyr Leu
                85                  90                  95

Trp Arg Leu Glu Ala Glu Lys Met Arg Leu Ala Glu Glu Glu Lys Leu
            100                 105                 110

Arg Lys Glu Met Ser Ala Lys Lys Ala Lys Glu Glu Ala Glu Arg Lys
        115                 120                 125

His Gln Glu Arg Leu Ala Gln Leu Ala Arg Glu Asp Ala Glu Arg Glu
    130                 135                 140

Leu Lys Glu Lys Glu Ala Ala Arg Arg Lys Lys Glu Leu Leu Glu Gln
145                 150                 155                 160

Met Glu Arg Ala Arg His Glu Pro Val Asn His Ser Asp Met Val Asp
                165                 170                 175

Lys Met Phe Gly Phe Leu Gly Thr Ser Gly Gly Leu Pro Gly Gln Glu
            180                 185                 190

Gly Gln Ala Pro Ser Gly Phe Glu Asp Leu Glu Arg Gly Arg Arg Glu
        195                 200                 205

Met Val Glu Glu Asp Leu Asp Ala Ala Leu Pro Leu Pro Asp Glu Asp
    210                 215                 220

Glu Glu Asp Ser Lys Tyr Val Val Ala Leu Gln Asp Asn Pro Asn Pro
225                 230                 235                 240

Ala Gly Glu Glu Ser Gly Phe Leu Ser Phe Ala Lys Gly Asp Leu Ile
                245                 250                 255

Ile Leu Asp His Asp Thr Gly Glu Gln Val Met Asn Ser Gly Trp Ala
            260                 265                 270

Asn Gly Ile Asn Glu Arg Thr Lys Gln Arg Gly Asp Phe Pro Thr Asp
        275                 280                 285

Ser Val Tyr Val Met Pro Thr Val Thr Met Pro Pro Arg Glu Ile Val
    290                 295                 300

Ala Leu Val Thr Met Thr Pro Asp Gln Arg Gln Asp Val Val Arg Leu
305                 310                 315                 320

Leu Gln Leu Arg Thr Ala Glu Pro Glu Val Arg Ala Lys Pro Tyr Thr
                325                 330                 335

Leu Glu Glu Phe Ser Tyr Asp Tyr Phe Arg Pro Pro Pro Lys His Thr
            340                 345                 350

Leu Ser Arg Val Met Val Ser Lys Ala Arg Gly Lys Asp Arg Leu Trp
        355                 360                 365
```

-continued

Ser His Thr Arg Glu Pro Leu Lys Gln Ala Leu Leu Lys Leu Leu
    370                 375                 380

Gly Ser Glu Glu Leu Ser Gln Glu Ala Cys Leu Ala Phe Ile Ala Val
385                 390                 395                 400

Leu Lys Tyr Met Gly Asp Tyr Pro Ser Lys Arg Thr Arg Ser Val Asn
                405                 410                 415

Glu Leu Thr Asp Gln Ile Phe Glu Gly Pro Leu Lys Ala Glu Pro Leu
            420                 425                 430

Lys Asp Glu Ala Tyr Val Gln Ile Leu Lys Gln Leu Thr Asp Asn His
        435                 440                 445

Ile Arg Tyr Ser Glu Glu Arg Gly Trp Glu Leu Leu Trp Leu Cys Thr
    450                 455                 460

Gly Leu Phe Pro Pro Ser Asn Ile Leu Leu Pro His Val Gln Arg Phe
465                 470                 475                 480

Leu Gln Ser Arg Lys His Cys Pro Leu Ala Ile Asp Cys Leu Gln Arg
                485                 490                 495

Leu Gln Lys Ala Leu Arg Asn Gly Ser Arg Lys Tyr Pro Pro His Leu
            500                 505                 510

Val Glu Val Glu Ala Ile Gln His Lys Thr Thr Gln Ile Phe His Lys
        515                 520                 525

Val Tyr Phe Pro Asp Asp Thr Asp Glu Ala Phe Glu Val Glu Ser Ser
    530                 535                 540

Thr Lys Ala Lys Asp Phe Cys Gln Asn Ile Ala Thr Arg Leu Leu Leu
545                 550                 555                 560

Lys Ser Ser Glu Gly Phe Ser Leu Phe Val Lys Ile Ala Asp Lys Val
                565                 570                 575

Leu Ser Val Pro Glu Asn Asp Phe Phe Phe Asp Phe Val Arg His Leu
            580                 585                 590

Thr Asp Trp Ile Lys Lys Ala Arg Pro Ile Lys Asp Gly Ile Val Pro
        595                 600                 605

Ser Leu Thr Tyr Gln Val Phe Phe Met Lys Lys Leu Trp Thr Thr Thr
    610                 615                 620

Val Pro Gly Lys Asp Pro Met Ala Asp Ser Ile Phe His Tyr Tyr Gln
625                 630                 635                 640

Glu Leu Pro Lys Tyr Leu Arg Gly Tyr His Lys Cys Thr Arg Glu Glu
                645                 650                 655

Val Leu Gln Leu Gly Ala Leu Ile Tyr Arg Val Lys Phe Glu Glu Asp
            660                 665                 670

Lys Ser Tyr Phe Pro Ser Ile Pro Lys Leu Leu Arg Glu Leu Val Pro
        675                 680                 685

Gln Asp Leu Ile Arg Gln Val Ser Pro Asp Asp Trp Lys Arg Ser Ile
    690                 695                 700

Val Ala Tyr Phe Asn Lys His Ala Gly Lys Ser Lys Glu Glu Ala Lys
705                 710                 715                 720

Leu Ala Phe Leu Lys Leu Ile Phe Lys Trp Pro Thr Phe Gly Ser Ala
                725                 730                 735

Phe Phe Glu Val Lys Gln Thr Thr Glu Pro Asn Phe Pro Glu Ile Leu
            740                 745                 750

Leu Ile Ala Ile Asn Lys Tyr Gly Val Ser Leu Ile Asp Pro Lys Thr
        755                 760                 765

Lys Asp Ile Leu Thr Thr His Pro Phe Thr Lys Ile Ser Asn Trp Ser
    770                 775                 780

-continued

```
Ser Gly Asn Thr Tyr Phe His Ile Thr Ile Gly Asn Leu Val Arg Gly
785                 790                 795                 800

Ser Lys Leu Leu Cys Glu Thr Ser Leu Gly Tyr Lys Met Asp Asp Leu
                805                 810                 815

Leu Thr Ser Tyr Ile Ser Gln Met Leu Thr Ala Met Ser Lys Gln Arg
                820                 825                 830

Gly Ser Arg Ser Gly Lys
                835

<210> SEQ ID NO 23
<211> LENGTH: 1153
<212> TYPE: PRT
<213> ORGANISM: Artificial Sequence
<220> FEATURE:
<223> OTHER INFORMATION: Synthetic Polypeptide

<400> SEQUENCE: 23

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
                20                  25                  30

Ser Gly Gln Val Gln Val Val Asp Asp Glu Asp Asn Glu His Trp Ile
            35                  40                  45

Ser Pro Gln Asn Ala Thr His Ile Lys Pro Met His Pro Thr Ser Val
50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
290                 295                 300
```

```
Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
            325                 330                 335

Thr Phe Glu Asn Leu Asp Ala Cys Glu Val Leu Phe Ser Pro Ser Leu
                340                 345                 350

Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
            435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Arg Leu Gln Ala Leu His Arg Ser Arg Lys Leu His
            500                 505                 510

Gln Gln Tyr Arg Leu Ala Arg Gln Arg Ile Ile Gln Phe Gln Ala Arg
            515                 520                 525

Cys Arg Ala Tyr Leu Val Arg Lys Ala Phe Arg His Arg Leu Trp Ala
530                 535                 540

Val Leu Thr Val Gln Ala Tyr Ala Arg Gly Met Ile Ala Arg Arg Leu
545                 550                 555                 560

His Gln Arg Leu Arg Ala Glu Tyr Leu Trp Arg Leu Glu Ala Glu Lys
                565                 570                 575

Met Arg Leu Ala Glu Glu Lys Leu Arg Lys Glu Met Ser Ala Lys
            580                 585                 590

Lys Ala Lys Glu Glu Ala Glu Arg Lys His Gln Glu Arg Leu Ala Gln
            595                 600                 605

Leu Ala Arg Glu Asp Ala Glu Arg Glu Leu Lys Glu Lys Glu Ala Ala
            610                 615                 620

Arg Arg Lys Lys Glu Leu Leu Glu Gln Met Glu Arg Ala Arg His Glu
625                 630                 635                 640

Pro Val Asn His Ser Asp Met Val Asp Lys Met Phe Gly Phe Leu Gly
                645                 650                 655

Thr Ser Gly Gly Leu Pro Gly Gln Glu Gly Gln Ala Pro Ser Gly Phe
            660                 665                 670

Glu Asp Leu Glu Arg Gly Arg Arg Glu Met Val Glu Glu Asp Leu Asp
            675                 680                 685

Ala Ala Leu Pro Leu Pro Asp Glu Asp Glu Asp Ser Glu Glu Leu
            690                 695                 700

Ser Gln Glu Ala Cys Leu Ala Phe Ile Ala Val Leu Lys Tyr Met Gly
705                 710                 715                 720

Asp Tyr Pro Ser Lys Arg Thr Arg Ser Val Asn Glu Leu Thr Asp Gln
```

```
                    725                 730                 735
Ile Phe Glu Gly Pro Leu Lys Ala Glu Pro Leu Lys Asp Glu Ala Tyr
                740                 745                 750
Val Gln Ile Leu Lys Gln Leu Thr Asp Asn His Ile Arg Tyr Ser Glu
                755                 760                 765
Glu Arg Gly Trp Glu Leu Leu Trp Leu Cys Thr Gly Leu Phe Pro Pro
            770                 775                 780
Ser Asn Ile Leu Leu Pro His Val Gln Arg Phe Leu Gln Ser Arg Lys
785                 790                 795                 800
His Cys Pro Leu Ala Ile Asp Cys Leu Gln Arg Leu Gln Lys Ala Leu
                805                 810                 815
Arg Asn Gly Ser Arg Lys Tyr Pro Pro His Leu Val Glu Val Glu Ala
                820                 825                 830
Ile Gln His Lys Thr Thr Gln Ile Phe His Lys Val Tyr Phe Pro Asp
                835                 840                 845
Asp Thr Asp Glu Ala Phe Glu Val Glu Ser Ser Thr Lys Ala Lys Asp
            850                 855                 860
Phe Cys Gln Asn Ile Ala Thr Arg Leu Leu Leu Lys Ser Ser Glu Gly
865                 870                 875                 880
Phe Ser Leu Phe Val Lys Ile Ala Asp Lys Val Leu Ser Val Pro Glu
                885                 890                 895
Asn Asp Phe Phe Phe Asp Phe Val Arg His Leu Thr Asp Trp Ile Lys
            900                 905                 910
Lys Ala Arg Pro Ile Lys Asp Gly Ile Val Pro Ser Leu Thr Tyr Gln
            915                 920                 925
Val Phe Phe Met Lys Lys Leu Trp Thr Thr Thr Val Pro Gly Lys Asp
        930                 935                 940
Pro Met Ala Asp Ser Ile Phe His Tyr Tyr Gln Glu Leu Pro Lys Tyr
945                 950                 955                 960
Leu Arg Gly Tyr His Lys Cys Thr Arg Glu Glu Val Leu Gln Leu Gly
                965                 970                 975
Ala Leu Ile Tyr Arg Val Lys Phe Glu Glu Asp Lys Ser Tyr Phe Pro
            980                 985                 990
Ser Ile Pro Lys Leu Leu Arg Glu Leu Val Pro Gln Asp Leu Ile Arg
            995                1000                1005
Gln Val Ser Pro Asp Asp Trp Lys Arg Ser Ile Val Ala Tyr Phe
        1010                1015                1020
Asn Lys His Ala Gly Lys Ser Lys Glu Glu Ala Lys Leu Ala Phe
        1025                1030                1035
Leu Lys Leu Ile Phe Lys Trp Pro Thr Phe Gly Ser Ala Phe Phe
        1040                1045                1050
Glu Val Lys Gln Thr Thr Glu Pro Asn Phe Pro Glu Ile Leu Leu
        1055                1060                1065
Ile Ala Ile Asn Lys Tyr Gly Val Ser Leu Ile Asp Pro Lys Thr
        1070                1075                1080
Lys Asp Ile Leu Thr Thr His Pro Phe Thr Lys Ile Ser Asn Trp
        1085                1090                1095
Ser Ser Gly Asn Thr Tyr Phe His Ile Thr Ile Gly Asn Leu Val
        1100                1105                1110
Arg Gly Ser Lys Leu Leu Cys Glu Thr Ser Leu Gly Tyr Lys Met
        1115                1120                1125
Asp Asp Leu Leu Thr Ser Tyr Ile Ser Gln Met Leu Thr Ala Met
        1130                1135                1140
```

-continued

```
Ser Lys Gln Arg Gly Ser Arg Ser Gly Lys
            1145                1150

<210> SEQ ID NO 24
<211> LENGTH: 811
<212> TYPE: PRT
<213> ORGANISM: Artificial Sequence
<220> FEATURE:
<223> OTHER INFORMATION: Synthetic Polypeptide

<400> SEQUENCE: 24

Arg Leu Gln Ala Leu His Arg Ser Arg Lys Leu His Gln Gln Tyr Arg
1               5                   10                  15

Leu Ala Arg Gln Arg Ile Ile Gln Phe Gln Ala Arg Cys Arg Ala Tyr
            20                  25                  30

Leu Val Arg Lys Ala Phe Arg His Arg Leu Trp Ala Val Leu Thr Val
        35                  40                  45

Gln Ala Tyr Ala Arg Gly Met Ile Ala Arg Arg Leu His Gln Arg Leu
    50                  55                  60

Arg Ala Glu Tyr Leu Trp Arg Leu Glu Ala Glu Lys Met Arg Leu Ala
65                  70                  75                  80

Glu Glu Glu Lys Leu Arg Lys Glu Met Ser Ala Lys Lys Ala Lys Glu
                85                  90                  95

Glu Ala Glu Arg Lys His Gln Glu Arg Leu Ala Gln Leu Ala Arg Glu
            100                 105                 110

Asp Ala Glu Arg Glu Leu Lys Glu Lys Glu Ala Ala Arg Arg Lys Lys
        115                 120                 125

Glu Leu Leu Glu Gln Met Glu Arg Ala Arg His Glu Pro Val Asn His
    130                 135                 140

Ser Asp Met Val Asp Lys Met Phe Gly Phe Leu Gly Thr Ser Gly Gly
145                 150                 155                 160

Leu Pro Gly Gln Glu Gly Gln Ala Pro Ser Gly Phe Glu Asp Leu Glu
                165                 170                 175

Arg Gly Arg Arg Glu Met Val Glu Glu Asp Leu Asp Ala Ala Leu Pro
            180                 185                 190

Leu Pro Asp Glu Asp Glu Glu Asp Ser Lys Tyr Val Val Ala Leu Gln
        195                 200                 205

Asp Asn Pro Asn Pro Ala Gly Glu Glu Ser Gly Phe Leu Ser Phe Ala
    210                 215                 220

Lys Gly Asp Leu Ile Ile Leu Asp His Asp Thr Gly Glu Gln Val Met
225                 230                 235                 240

Asn Ser Gly Trp Ala Asn Gly Ile Asn Glu Arg Thr Lys Gln Arg Gly
                245                 250                 255

Asp Phe Pro Thr Asp Ser Val Tyr Val Met Pro Thr Val Thr Met Pro
            260                 265                 270

Pro Arg Glu Ile Val Ala Leu Val Thr Met Thr Pro Asp Gln Arg Gln
        275                 280                 285

Asp Val Val Arg Leu Leu Gln Leu Arg Thr Ala Glu Pro Glu Val Arg
    290                 295                 300

Ala Lys Pro Tyr Thr Leu Glu Glu Phe Ser Tyr Asp Tyr Phe Arg Pro
305                 310                 315                 320

Pro Pro Lys His Thr Leu Ser Arg Val Met Val Ser Lys Ala Arg Gly
                325                 330                 335

Lys Asp Arg Leu Trp Ser His Thr Arg Glu Pro Leu Lys Gln Ala Leu
            340                 345                 350
```

Leu Lys Lys Leu Leu Gly Ser Glu Glu Leu Ser Gln Glu Ala Cys Leu
        355                 360                 365

Ala Phe Ile Ala Val Leu Lys Tyr Met Gly Asp Tyr Pro Ser Lys Arg
    370                 375                 380

Thr Arg Ser Val Asn Glu Leu Thr Asp Gln Ile Phe Glu Gly Pro Leu
385                 390                 395                 400

Lys Ala Glu Pro Leu Lys Asp Glu Ala Tyr Val Gln Ile Leu Lys Gln
                405                 410                 415

Leu Thr Asp Asn His Ile Arg Tyr Ser Glu Glu Arg Gly Trp Glu Leu
                420                 425                 430

Leu Trp Leu Cys Thr Gly Leu Phe Pro Pro Ser Asn Ile Leu Leu Pro
        435                 440                 445

His Val Gln Arg Phe Leu Gln Ser Arg Lys His Cys Pro Leu Ala Ile
    450                 455                 460

Asp Cys Leu Gln Arg Leu Gln Lys Ala Leu Arg Asn Gly Ser Arg Lys
465                 470                 475                 480

Tyr Pro Pro His Leu Val Glu Val Glu Ala Ile Gln His Lys Thr Thr
                485                 490                 495

Gln Ile Phe His Lys Val Tyr Phe Pro Asp Asp Thr Asp Glu Ala Phe
                500                 505                 510

Glu Val Glu Ser Ser Thr Lys Ala Lys Asp Phe Cys Gln Asn Ile Ala
        515                 520                 525

Thr Arg Leu Leu Leu Lys Ser Ser Glu Gly Phe Ser Leu Phe Val Lys
    530                 535                 540

Ile Ala Asp Lys Val Leu Ser Val Pro Glu Asn Asp Phe Phe Phe Asp
545                 550                 555                 560

Phe Val Arg His Leu Thr Asp Trp Ile Lys Lys Ala Arg Pro Ile Lys
                565                 570                 575

Asp Gly Ile Val Pro Ser Leu Thr Tyr Gln Val Phe Phe Met Lys Lys
                580                 585                 590

Leu Trp Thr Thr Thr Val Pro Gly Lys Asp Pro Met Ala Asp Ser Ile
        595                 600                 605

Phe His Tyr Tyr Gln Glu Leu Pro Lys Tyr Leu Arg Gly Tyr His Lys
    610                 615                 620

Cys Thr Arg Glu Glu Val Leu Gln Leu Gly Ala Leu Ile Tyr Arg Val
625                 630                 635                 640

Lys Phe Glu Glu Asp Lys Ser Tyr Phe Pro Ser Ile Pro Lys Leu Leu
                645                 650                 655

Arg Glu Leu Val Pro Gln Asp Leu Ile Arg Gln Val Ser Pro Asp Asp
                660                 665                 670

Trp Lys Arg Ser Ile Val Ala Tyr Phe Asn Lys His Ala Gly Lys Ser
        675                 680                 685

Lys Glu Glu Ala Lys Leu Ala Phe Leu Lys Leu Ile Phe Lys Trp Pro
    690                 695                 700

Thr Phe Gly Ser Ala Phe Phe Glu Val Lys Gln Thr Thr Glu Pro Asn
705                 710                 715                 720

Phe Pro Glu Ile Leu Leu Ile Ala Ile Asn Lys Tyr Gly Val Ser Leu
                725                 730                 735

Ile Asp Pro Lys Thr Lys Asp Ile Leu Thr Thr His Pro Phe Thr Lys
                740                 745                 750

Ile Ser Asn Trp Ser Ser Gly Asn Thr Tyr Phe His Ile Thr Ile Gly
        755                 760                 765

Asn Leu Val Arg Gly Ser Lys Leu Leu Cys Glu Thr Ser Leu Gly Tyr
770                 775                 780

Lys Met Asp Asp Leu Leu Thr Ser Tyr Ile Ser Gln Met Leu Thr Ala
785                 790                 795                 800

Met Ser Lys Gln Arg Gly Ser Arg Ser Gly Lys
                    805                 810

<210> SEQ ID NO 25
<211> LENGTH: 638
<212> TYPE: PRT
<213> ORGANISM: Artificial Sequence
<220> FEATURE:
<223> OTHER INFORMATION: Synthetic Polypeptide

<400> SEQUENCE: 25

Arg Ser Asn Phe Leu Lys Leu Lys Asn Ala Ala Thr Leu Ile Gln Arg
1               5                   10                  15

His Trp Arg Gly His Asn Cys Arg Lys Asn Tyr Ser Lys Tyr Val Val
            20                  25                  30

Ala Leu Gln Asp Asn Pro Asn Pro Ala Gly Glu Ser Gly Phe Leu
        35                  40                  45

Ser Phe Ala Lys Gly Asp Leu Ile Ile Leu Asp His Asp Thr Gly Glu
50                  55                  60

Gln Val Met Asn Ser Gly Trp Ala Asn Gly Ile Asn Glu Arg Thr Lys
65                  70                  75                  80

Gln Arg Gly Asp Phe Pro Thr Asp Ser Val Tyr Val Met Pro Thr Val
                85                  90                  95

Thr Met Pro Pro Arg Glu Ile Val Ala Leu Val Thr Met Thr Pro Asp
            100                 105                 110

Gln Arg Gln Asp Val Val Arg Leu Leu Gln Leu Arg Thr Ala Glu Pro
        115                 120                 125

Glu Val Arg Ala Lys Pro Tyr Thr Leu Glu Glu Phe Ser Tyr Asp Tyr
130                 135                 140

Phe Arg Pro Pro Pro Lys His Thr Leu Ser Arg Val Met Val Ser Lys
145                 150                 155                 160

Ala Arg Gly Lys Asp Arg Leu Trp Ser His Thr Arg Glu Pro Leu Lys
                165                 170                 175

Gln Ala Leu Leu Lys Lys Leu Leu Gly Ser Glu Glu Leu Ser Gln Glu
            180                 185                 190

Ala Cys Leu Ala Phe Ile Ala Val Leu Lys Tyr Met Gly Asp Tyr Pro
        195                 200                 205

Ser Lys Arg Thr Arg Ser Val Asn Glu Leu Thr Asp Gln Ile Phe Glu
210                 215                 220

Gly Pro Leu Lys Ala Glu Pro Leu Lys Asp Glu Ala Tyr Val Gln Ile
225                 230                 235                 240

Leu Lys Gln Leu Thr Asp Asn His Ile Arg Tyr Ser Glu Glu Arg Gly
                245                 250                 255

Trp Glu Leu Leu Trp Leu Cys Thr Gly Leu Phe Pro Pro Ser Asn Ile
            260                 265                 270

Leu Leu Pro His Val Gln Arg Phe Leu Gln Ser Arg Lys His Cys Pro
        275                 280                 285

Leu Ala Ile Asp Cys Leu Gln Arg Leu Gln Lys Ala Leu Arg Asn Gly
290                 295                 300

Ser Arg Lys Tyr Pro Pro His Leu Val Glu Val Glu Ala Ile Gln His
305                 310                 315                 320

Lys Thr Thr Gln Ile Phe His Lys Val Tyr Phe Pro Asp Asp Thr Asp
            325                 330                 335

Glu Ala Phe Glu Val Glu Ser Ser Thr Lys Ala Lys Asp Phe Cys Gln
            340                 345                 350

Asn Ile Ala Thr Arg Leu Leu Leu Lys Ser Ser Glu Gly Phe Ser Leu
            355                 360                 365

Phe Val Lys Ile Ala Asp Lys Val Leu Ser Val Pro Glu Asn Asp Phe
            370                 375                 380

Phe Phe Asp Phe Val Arg His Leu Thr Asp Trp Ile Lys Lys Ala Arg
385                 390                 395                 400

Pro Ile Lys Asp Gly Ile Val Pro Ser Leu Thr Tyr Gln Val Phe Phe
            405                 410                 415

Met Lys Lys Leu Trp Thr Thr Thr Val Pro Gly Lys Asp Pro Met Ala
            420                 425                 430

Asp Ser Ile Phe His Tyr Tyr Gln Glu Leu Pro Lys Tyr Leu Arg Gly
            435                 440                 445

Tyr His Lys Cys Thr Arg Glu Glu Val Leu Gln Leu Gly Ala Leu Ile
            450                 455                 460

Tyr Arg Val Lys Phe Glu Glu Asp Lys Ser Tyr Phe Pro Ser Ile Pro
465                 470                 475                 480

Lys Leu Leu Arg Glu Leu Val Pro Gln Asp Leu Ile Arg Gln Val Ser
            485                 490                 495

Pro Asp Asp Trp Lys Arg Ser Ile Val Ala Tyr Phe Asn Lys His Ala
            500                 505                 510

Gly Lys Ser Lys Glu Glu Ala Lys Leu Ala Phe Leu Lys Leu Ile Phe
            515                 520                 525

Lys Trp Pro Thr Phe Gly Ser Ala Phe Phe Glu Val Lys Gln Thr Thr
530                 535                 540

Glu Pro Asn Phe Pro Glu Ile Leu Leu Ile Ala Ile Asn Lys Tyr Gly
545                 550                 555                 560

Val Ser Leu Ile Asp Pro Lys Thr Lys Asp Ile Leu Thr Thr His Pro
            565                 570                 575

Phe Thr Lys Ile Ser Asn Trp Ser Ser Gly Asn Thr Tyr Phe His Ile
            580                 585                 590

Thr Ile Gly Asn Leu Val Arg Gly Ser Lys Leu Leu Cys Glu Thr Ser
            595                 600                 605

Leu Gly Tyr Lys Met Asp Asp Leu Leu Thr Ser Tyr Ile Ser Gln Met
            610                 615                 620

Leu Thr Ala Met Ser Lys Gln Arg Gly Ser Arg Ser Gly Lys
625                 630                 635

<210> SEQ ID NO 26
<211> LENGTH: 763
<212> TYPE: PRT
<213> ORGANISM: Artificial Sequence
<220> FEATURE:
<223> OTHER INFORMATION: Synthetic Polypeptide

<400> SEQUENCE: 26

Arg Ser Asn Phe Leu Lys Leu Lys Asn Ala Ala Thr Leu Ile Gln Arg
1               5                   10                  15

His Trp Arg Gly His Asn Cys Arg Lys Asn Tyr Arg Leu Gln Ala Leu
            20                  25                  30

His Arg Ser Arg Lys Leu His Gln Gln Tyr Arg Leu Ala Arg Gln Arg
        35                  40                  45

-continued

```
Ile Ile Gln Phe Gln Ala Arg Cys Arg Ala Tyr Leu Val Arg Lys Ala
 50                  55                  60
Phe Arg His Arg Leu Trp Ala Val Leu Thr Val Gln Ala Tyr Ala Arg
 65                  70                  75                  80
Gly Met Ile Ala Arg Arg Leu His Gln Arg Leu Arg Ala Glu Tyr Leu
                 85                  90                  95
Trp Arg Leu Glu Ala Glu Lys Met Arg Leu Ala Glu Glu Glu Lys Leu
                100                 105                 110
Arg Lys Glu Met Ser Ala Lys Lys Ala Lys Glu Glu Ala Glu Arg Lys
                115                 120                 125
His Gln Glu Arg Leu Ala Gln Leu Ala Arg Glu Asp Ala Glu Arg Glu
130                 135                 140
Leu Lys Glu Lys Glu Ala Ala Arg Arg Lys Lys Glu Leu Leu Glu Gln
145                 150                 155                 160
Met Glu Arg Ala Arg His Glu Pro Val Asn His Ser Asp Met Val Asp
                165                 170                 175
Lys Met Phe Gly Phe Leu Gly Thr Ser Gly Gly Leu Pro Gly Gln Glu
                180                 185                 190
Gly Gln Ala Pro Ser Gly Phe Glu Asp Leu Glu Arg Gly Arg Arg Glu
                195                 200                 205
Met Val Glu Glu Asp Leu Asp Ala Ala Leu Pro Leu Pro Asp Glu Asp
210                 215                 220
Glu Glu Asp Tyr Thr Arg Arg Pro Leu Lys Gln Pro Leu Leu Tyr His
225                 230                 235                 240
Asp Asp Glu Gly Asp Gln Leu Ala Ala Leu Ala Val Trp Ile Thr Ile
                245                 250                 255
Leu Arg Phe Met Gly Asp Leu Pro Glu Pro Lys Tyr His Thr Ala Met
                260                 265                 270
Ser Asp Gly Ser Glu Lys Ile Pro Val Met Thr Lys Ile Tyr Glu Thr
                275                 280                 285
Leu Gly Lys Lys Thr Tyr Lys Arg Glu Leu Gln Ala Leu Gln Gly Glu
                290                 295                 300
Gly Glu Ala Gln Leu Pro Glu Gly Gln Lys Lys Ser Ser Val Arg His
305                 310                 315                 320
Lys Leu Val His Leu Thr Leu Lys Lys Ser Lys Leu Thr Glu Glu
                325                 330                 335
Val Thr Lys Arg Leu His Asp Gly Glu Ser Thr Val Gln Gly Asn Ser
                340                 345                 350
Met Leu Glu Asp Arg Pro Thr Ser Asn Leu Glu Lys Leu His Phe Ile
                355                 360                 365
Ile Gly Asn Gly Ile Leu Arg Pro Ala Leu Arg Asp Glu Ile Tyr Cys
                370                 375                 380
Gln Ile Ser Lys Gln Leu Thr His Asn Pro Ser Lys Ser Ser Tyr Ala
385                 390                 395                 400
Arg Gly Trp Ile Leu Val Ser Leu Cys Val Gly Cys Phe Ala Pro Ser
                405                 410                 415
Glu Lys Phe Val Lys Tyr Leu Arg Asn Phe Ile His Gly Gly Pro Pro
                420                 425                 430
Gly Tyr Ala Pro Tyr Cys Glu Arg Leu Arg Arg Thr Phe Val Asn
                435                 440                 445
Gly Thr Arg Thr Gln Pro Pro Ser Trp Leu Glu Leu Gln Ala Thr Lys
450                 455                 460
Ser Lys Lys Pro Ile Met Leu Ser Lys Tyr Val Val Ala Leu Gln Asp
```

```
                        465                 470                 475                 480
Asn Pro Asn Pro Ala Gly Glu Glu Ser Gly Phe Leu Ser Phe Ala Lys
                485                 490                 495
Gly Asp Leu Ile Ile Leu Asp His Asp Thr Gly Glu Gln Val Met Asn
                500                 505                 510
Ser Gly Trp Ala Asn Gly Ile Asn Glu Arg Thr Lys Gln Arg Gly Asp
                515                 520                 525
Phe Pro Thr Asp Ser Val Tyr Val Met Pro Thr Val Thr Met Pro Pro
                530                 535                 540
Arg Glu Ile Val Ala Leu Val Thr Met Thr Pro Asp Gln Arg Gln Asp
545                 550                 555                 560
Val Val Arg Leu Leu Gln Leu Arg Thr Ala Glu Pro Glu Val Arg Ala
                565                 570                 575
Lys Pro Tyr Thr Leu Glu Glu Phe Ser Tyr Asp Tyr Phe Arg Pro Pro
                580                 585                 590
Pro Lys His Thr Leu Ser Arg Val Met Val Ser Lys Ala Arg Gly Lys
                595                 600                 605
Asp Arg Leu Trp Ser His Thr Arg Glu Pro Leu Lys Gln Ala Leu Leu
        610                 615                 620
Lys Lys Leu Leu Gly Ser Glu Glu Leu Ser Gln Glu Ala Cys Leu Ala
625                 630                 635                 640
Phe Ile Ala Val Leu Lys Tyr Met Gly Asp Tyr Pro Ser Lys Arg Thr
                645                 650                 655
Arg Ser Val Asn Glu Leu Thr Asp Gln Ile Phe Glu Gly Pro Leu Lys
                660                 665                 670
Ala Glu Pro Leu Lys Asp Glu Ala Tyr Val Gln Ile Leu Lys Gln Leu
        675                 680                 685
Thr Asp Asn His Ile Arg Tyr Ser Glu Glu Arg Gly Trp Glu Leu Leu
        690                 695                 700
Trp Leu Cys Thr Gly Leu Phe Pro Pro Ser Asn Ile Leu Leu Pro His
705                 710                 715                 720
Val Gln Arg Phe Leu Gln Ser Arg Lys His Cys Pro Leu Ala Ile Asp
                725                 730                 735
Cys Leu Gln Arg Leu Gln Lys Ala Leu Arg Asn Gly Ser Arg Lys Tyr
                740                 745                 750
Pro Pro His Leu Val Glu Val Glu Ala Ile Gln
        755                 760
```